US008685456B2

(12) United States Patent
Beumer et al.

(10) Patent No.: US 8,685,456 B2
(45) Date of Patent: *Apr. 1, 2014

(54) TOPICAL COMPOSITIONS COMPRISING NANOPARTICLES OF AN ISOFLAVONE

(75) Inventors: Raphael Beumer, Loerrach (DE); Chyi-Cheng Chen, Binningen (CH); Heinz Gutzwiller, Brislach (CH); Philippe Emmanuel Maillan, Eschentzwiller (FR); Markus Nowotny, Muttenz (CA); Bernd Schlegel, Rheinfelden (DE); Juergen H. Vollhardt, Ramlinsburg (CH)

(73) Assignee: DSM IP Assets B.V., Heerlen (NL)

( * ) Notice: Subject to any disclaimer, the term of this patent is extended or adjusted under 35 U.S.C. 154(b) by 1239 days.

This patent is subject to a terminal disclaimer.

(21) Appl. No.: 11/994,212

(22) PCT Filed: Jan. 31, 2006

(86) PCT No.: PCT/EP2006/000826
§ 371 (c)(1),
(2), (4) Date: Apr. 10, 2008

(87) PCT Pub. No.: WO2007/000192
PCT Pub. Date: Jan. 4, 2007

(65) Prior Publication Data
US 2008/0311209 A1 Dec. 18, 2008

(30) Foreign Application Priority Data

Jun. 29, 2005 (EP) .................................... 05014094

(51) Int. Cl.
*A61Q 19/00* (2006.01)
*A61Q 17/04* (2006.01)
*A61Q 19/02* (2006.01)
*A61Q 19/08* (2006.01)
*A61K 8/02* (2006.01)
*A61Q 17/00* (2006.01)
*A61K 8/34* (2006.01)
*A61K 8/49* (2006.01)
*A61K 8/73* (2006.01)

(52) U.S. Cl.
CPC .............. *A61Q 19/00* (2013.01); *A61Q 17/005* (2013.01); *A61Q 17/04* (2013.01); *A61Q 19/08* (2013.01); *A61Q 19/02* (2013.01); *A61K 8/0241* (2013.01); *A61K 8/347* (2013.01); *A61K 8/498* (2013.01); *A61K 8/732* (2013.01); *Y10S 977/926* (2013.01)

USPC ............ 424/489; 424/59; 514/773; 514/774; 514/775; 514/777; 514/778; 514/779; 514/781; 977/926

(58) Field of Classification Search
None
See application file for complete search history.

(56) References Cited

U.S. PATENT DOCUMENTS

| | | | |
|---|---|---|---|
| 5,824,702 A * | 10/1998 | Wei | 514/456 |
| 6,251,420 B1 * | 6/2001 | Miljkovic | 424/439 |
| 6,677,386 B1 * | 1/2004 | Giezen et al. | 516/31 |
| 2002/0107282 A1 * | 8/2002 | Chevalier et al. | 514/486 |
| 2002/0110599 A1 | 8/2002 | Auweter et al. | |
| 2002/0142017 A1 | 10/2002 | Simonnet | |
| 2002/0197288 A1 | 12/2002 | Chevalier | |
| 2005/0202140 A1 * | 9/2005 | Corbin et al. | 426/489 |

FOREIGN PATENT DOCUMENTS

| | | |
|---|---|---|
| EP | 1 477 152 | 11/2004 |
| FR | 2 817 478 | 6/2002 |
| WO | 2004/022027 | 3/2004 |
| WO | 2004/112689 | 12/2004 |
| WO | 2005/025529 | 3/2005 |
| WO | 2005/025530 | 3/2005 |

OTHER PUBLICATIONS

MS Cardinali, TYF Lam. "New Advances in Starch-Based Particle Technologies for Aesthetic Modification." www.personalcarepolymers.com, Presented at PCIA Manila—Mar. 2003, 11 total pages (cover page plus pp. 1-10).*

FI Kanaze, E Kokkalou, I Niopas, M Georgarakis, A Stergiou, D Bikiaris. "Thermal Analysis Study of Flavonoid Solid Dispersions Having Enhanced Solubility." Journal of Thermal Analysis and Calorimetry, vol. 83 Issue 2, 2006, pp. 283-290.*

Muller et al., "Nanosuspensions as particulate drug formulations in therapy rationale for development and what we can expect for the future", *Advanced Drug Delivery Reviews*, vol. 47, 2001, pp. 3-19, XP002373513.

International Preliminary Report mailed Jan. 30, 2008 in PCT/EP2006/000826.

Written Opinion of the International Searching Authority Report mailed Jan. 30, 2008 in PCT/EP2006/000826.

* cited by examiner

*Primary Examiner* — Frederick Krass
*Assistant Examiner* — Isaac Shomer
(74) *Attorney, Agent, or Firm* — Nixon & Vanderhye P.C.

(57) ABSTRACT

The present invention is directed to topical compositions, comprising isoflavone nanoparticle compositions. The isoflavone nanoparticle compositions contain isoflavone in the form of nanoparticles and preferably a carrier. In the topical compositions recrystallization of the isoflavone to bigger particles is avoided.

26 Claims, 16 Drawing Sheets

TOPICAL COMPOSITIONS COMPRISING NANOPARTICLES OF AN ISOFLAVONE

This application is the U.S. national phase of International Application No. PCT/EP2006/000826 filed 31 Jan. 2006 which designated the U.S. and claims priority to European Patent Application No. 05014094.6 filed 29 Jun. 2005, the entire contents of each of which are hereby incorporated by reference.

The present invention is directed to topical compositions comprising an isoflavone. The topical compositions comprise an isoflavone nanoparticle composition comprising the isoflavone in the form of nanoparticles and optionally a carrier. The topical compositions are particularly cosmetic compositions or pharmaceutical compositions. In the topical compositions comprising the isoflavone nanoparticle compositions recrystallization of the isoflavone to bigger particles is retarded. The isoflavone is preferably genistein.

Isoflavones are a group of vegetable dyes belonging to the flavonoids and are derived from isoflavone. The following isoflavones are particularly important:

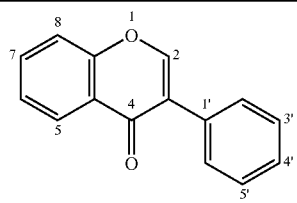

|   |            | 5  | 7    | 3' | 4'   |
|---|------------|----|------|----|------|
| 1 | Isoflavone | H  | H    | H  | H    |
| 2 | Daidzein   | H  | OH   | H  | OH   |
| 3 | Genistein  | OH | OH   | H  | OH   |
| 4 | Prunetin   | OH | OCH$_3$ | H  | OH   |
| 5 | Biochanin A| OH | OH   | H  | OCH$_3$ |
| 6 | Orobol     | OH | OH   | OH | OH   |
| 7 | Santal     | OH | OCH$_3$ | OH | OH   |
| 8 | Pratensein | OH | OH   | OH | OCH3 |

One of the most important isoflavones is genistein.

Genistein is a well-known pharmaceutically and cosmetically active ingredient which has anti-bacterial activity. Genistein is a calmodulin-antagonist, and of particular importance is the enzyme-inhibitory activity of genistein e.g. against tyrosine kinases, dopa-carboxylases, etc. Genistein can also be used in insecticides. The chemical name of genistein is 4',5,7-trihydroxyisoflavone, and the compound can be obtained by purification from natural products, such as soy products (e.g. Biochem. Biophys. Res. Commun. 179: 661-667, 1991), but it can also be chemically synthesized by methods known in the art. Genistein is commercially available from many suppliers and in a high purity. The chemical structure of genistein is as follows:

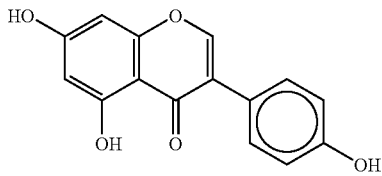

A significant number of publications are directed to genistein and the use thereof, and it can e.g. be referred to U.S. Pat. No. 5,824,702, WO 03/068218 or U.S. Pat. No. 5,948,814, to mention only three recent ones of the numerous patents and patent applications in this field.

Genistein is normally produced in crystalline powder form e.g. according to a process as disclosed in WO 2004/009576. Such a powder form has a very poor flowability. The poor powder flowability renders the crystalline powder difficult for use in making tablets and other application forms that require the powder to be free flowing. The same problem occurs if one tries to make formulations with other isoflavones.

Despite the numerous documents describing genistein and its applications, the presently marketed topical compositions with genistein either contain only very low concentrations of genistein, such as 0.01 wt.-% or less, or contain an organic solubilizer or solvent for genistein, such as ethanol. The presence of organic solvents such as ethanol in topical compositions should, however, be avoided, if possible, since organic solvents can cause skin irritations. Anyway, even in the presence of organic solubilizers only a rather small amount of genistein can be incorporated into cosmetic compositions.

If one prepares a topical composition which is solely based on water as a solvent and contains higher concentrations of commercially available genistein, such as more than 0.1 wt.-%, in particular more than 0.2 wt.-% or 0.5 wt.-% or more genistein, such a topical composition becomes gritty during storage. Applying such a gritty topical composition to the skin can cause irritations, and the consumer acceptance is low, in particular, if the composition is a cosmetic composition. Furthermore, together with becoming gritty the activity of the genistein in the aqueous topical formulation can decrease upon storage.

Nanosuspensions of water-insoluble pharmaceutically active compounds and methods of preparing such nanosuspensions are known in the art, and it can be referred e.g. to U.S. Pat. No. 5,858,410 and U.S. Pat. No. 5,145,684. These documents disclose many possible active ingredients which can be provided in the form of nanosuspensions, but they are quiet on genistein. Both documents are mainly concerned with a method to increase the bioavailability of a drug, and they do not address topical compositions and problems which occur in topical compositions.

Furthermore, there exist several review articles on drug nanoparticles or micron-sized drug particles, e.g. "Advanced Drug Delivery Reviews 47 (2001) 3-19". This document discloses that providing a drug in the form of nanoparticles might increase the saturation solubility and the dissolution velocity of the drug. The document is mainly concerned with the bioavailability of water-insoluble drugs which are for oral or parenteral administration. Topical formulations and problems which might occur in topical formulations are not disclosed. Genistein is not disclosed.

Another review article "Pharmaceutical Development and Technology, Vol. 9, No. 1, pages 1-13, 2004" compares the different processes for producing micron-sized drug particles and their advantages and disadvantages. According to the document, the production of small dry particles is still a challenge, and some problems are discussed which occur, in particular if the small particles are prepared by comminution of bigger dry particles and not by association of molecularly dispersed drug. While the document generally mentions that micronized drugs can be used for intravenous, topical, oral or ophthalmic compositions, the main focus is on pulmonary dry administration and improvement of the bioavailability of poorly water-soluble drugs. Apart from the above general information, topical compositions are not mentioned and genistein is not mentioned either.

WO 99/38509 discloses micelles which are formed by coupling e.g. genistein with an amphiphilic carrier. The micelles have an average diameter of about 100 nm and are suitable for food supplements. The amphiphilic carriers disclosed in this document are essentially polyethyleneglycolyzed fatty acid glycerides such as those obtained from fully or partially hydrogenated various vegetable oils. WO 99/38509 does not disclose topical compositions or cosmetic compositions or problems which occur in topical compositions.

A particular problem with the utilization of micronized materials for topical application is the possibility of recrystallisation of such materials when exposed to temperature differences. These temperature differences can cause some materials to recrystallize and thereby forming again gritty unacceptable formulations with large crystals.

The object of the present invention is to provide topical aqueous compositions, in particular topical aqueous cosmetic compositions, more preferable crèmes and emulsions, which are preferably free of ethanol and preferably also of other organic solvents, and which contain isoflavone, in particular genistein, in a high concentration of 0.01 wt.-% or more, but preferably even much higher than that, such as 0.3 wt.-% or more. The compositions should be stable during storage for at least three months, preferably for at least six months, more preferably for at least one year and not develop grittiness during this time. The formulation structure should also be persistent against temperature changes and able to pass the "swing" test.

This object is achieved on the basis of the unexpected finding that compositions comprising nanoparticles having an average particle size D[4,3] as determined by laser diffraction technique of less than 3 μm of an isoflavone, such as genistein and optionally a carrier and optionally water can be incorporated into topical aqueous compositions to provide a high concentration of the isoflavone in the topical composition and that these topical compositions do not become gritty upon storage. The activity of the isoflavone (the genistein) in these topical compositions does not decrease either during storage. The compositions of nanoparticles of isoflavone and optionally a carrier are preferably obtained by homogenizing a mixture of isoflavone and the carrier under high pressure. A particularly preferred process to obtain compostions of nanoparticles of isoflavone and optionally a carrier is a milling process in an agitated bead mill.

DETAILED DESCRIPTION

Figure 1:
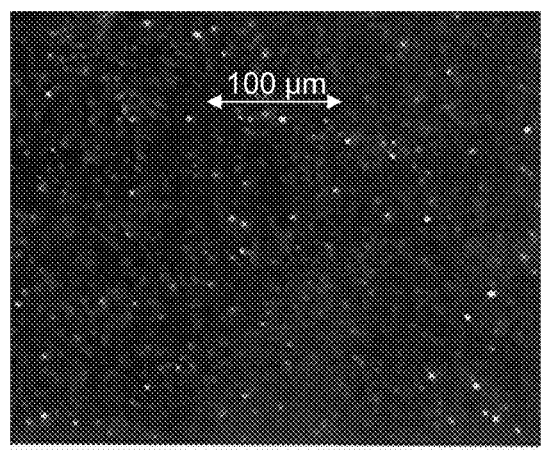
FIGS. 1 and 2 are photomicrographs of formulations after six months of storage at room temperature which employ stabilized nanoparticles of genistein according to an embodiment of the invention and conventional genistein as described below in Example 8 by formulations #1 and #2, respectively.

The compositions comprising nanoparticles of isoflavone, optionally a carrier and optionally water, which have been found useful in the present invention and wherein the isoflavone has an average particle size D[4,3] as determined by laser diffraction technique of less than 3 μm will be referred to as isoflavone (or genistein) nanoparticle compositions in order to distinguish these compositions from the topical compositions and in particular from the topical pharmaceutical and cosmetic compositions of the present invention.

The present invention thus provides topical compositions, in particular topical pharmaceutical compositions and topical cosmetic compositions, which are preferably free of ethanol, containing the isoflavone nanoparticle compositions. The present invention also provides isoflavone nanoparticle compositions and a process for producing those isoflavone nanoparticle compositions.

While the process for preparing these isoflavone nanoparticle compositions is not particularly limited, the isoflavone nanoparticle compositions are preferably prepared by a high pressure homogenization process, wherein a mixture of an isoflavone, which is preferably crystalline, optionally the carrier and water is subjected to a high pressure homogenizer. Particularly preferred is a process in which a mixture of an isoflavone, which is preferably crystalline, optionally the carrier and water is subjected to an agitated bead mill. Optionally the resulting suspension is subjected to a drying process The isoflavone nanoparticle compositions contain the isoflavone nanoparticles and optionally a carrier and, immediately after their preparation, usually water, however, it is possible to remove the water. Preferably, the compositions consist essentially (i) of the isoflavone nanoparticles or
(ii) of the isoflavone nanoparticles and water or
(iii) of the isoflavone nanoparticles and a carrier or
(iv) of the isoflavone nanoparticles and water and a carrier.

"Consisting essentially of" means that not more than 10%, preferably not more than 5% more preferably not more than 2% other components than the specified components are present in the compositions.

The isoflavones are preferably not in the form of micelles as disclosed in WO 99/38509, as such micelles are not formed by the preferred processes of the present invention and the carrier used according to the invention is preferably not an amphiphilic lipid carrier of the type disclosed in WO 99/38509, i.e. a saturated or monounsaturated polyethyleneglycolyzed fatty acid glyceride.

The invention will be further described for genistein which is the most preferred isoflavone of the present invention. However, the further description is also valid for the other isoflavones covered by the present invention. It is of course also possible to use a mixture of more than one isoflavone, e.g. of genistein and one or more further isoflavones. The term "isoflavone" as used herein is meant to encompass all those possibilities.

The topical compositions and in particular the topical pharmaceutical compositions and topical cosmetic compositions can advantageously be used for all applications where genistein can be used topically. Because of the high stability of the genistein in the compositions and the high concentration in which genistein can be included within the compositions of the present invention, the topical compositions of the present invention are advantageous in all known application fields of genistein.

Particularly preferred is the use of the topical cosmetic and pharmaceutical compositions of the present invention for achieving a beautifying effect on human skin, in particular an anti-aging effect or a skin lightening effect. Furthermore preferred is the use of the topical cosmetic and pharmaceutical compositions of the present invention as anti-wrinkle compositions, in particular the compositions can be used for wrinkle treatment and wrinkle prevention.

Furthermore, it is known that genistein can protect the skin and the hair against UV-radiation and can even repair damaged skin. Thus, the topical cosmetic and pharmaceutical compositions of the present invention are also preferably compositions for use in protecting against UV-radiation damages or repairing damaged skin, in particular skin which has been damaged by UV-radiation. For those application fields the topical cosmetic and pharmaceutical compositions of the present invention preferably additionally contain one or more further sunscreen agents.

A further preferred field of use is the use for the treatment of hypersensitive skin, wherein genistein is also widely used. Other fields of use are the treatment of hyperpigmented skin, of cellulite, acne, etc.

The uses of genistein either alone or in combination with other active ingredients are described in many documents, e.g. in the following documents: DE 103 01 632, DE 103 01 631, US 2004/034,098, EP 1 243 254, EP 1 104 672, U.S. Pat. No. 6,060,070, U.S. Pat. No. 6,130,254, US 2002/160,965, US 2003/027,772, WO 2004/000242, DE 102 11 192, US 2003/044,438, US 2004/072,764, US 2002/048,798, US 2004/071745, KR 2001/001290, EP 1 508 328, EP 1 473 028, WO 03/051287, US 2003/103,954, WO 02/00183, WO 99/51220, U.S. Pat. No. 6,455,032, US 2005/058,709, U.S. Pat. No. 5,824,702, US 2002/099,095, EP 1 300 138, DE 101 21 375, U.S. Pat. No. 5,952,373, WO 2005/030157, FR 2 859 629, US 2005/037,099, FR 2 856 294, WO 2004/062,635, FR 2 845 900, US 2005/142,081, US 2002/106,388, US 2004/170,655, US 2002/107,282, EP 1 201 227, DE 100 09 424, EP 0 829 261, DE 44 32 947 and JP 60061513. With respect to the advantageous fields of use of the topical cosmetic and pharmaceutical compositions of the present invention and with respect to combinations of genistein with other active ingredients, it is explicitly referred to the above documents which are also included herein by reference. Since the compositions of the present invention contain particularly high concentrations of genistein in a particularly advantageous form, all positive effects which are described in those documents in connection with the use of genistein of course also occur (even to a higher degree) with the genistein compositions of the present invention.

The topical cosmetic and pharmaceutical compositions of the present invention can preferably be used for restructuring and rejuvenating the skin, delaying the decrease in the collagen in naturally-aged human skin, for the treatment of signs of aging of the skin, for providing an estrogenic collagen synthesis stimulating anti-oxidant and radical scavenging action, for inhibiting photoaging of the skin and as anti-oxidant compositions.

Furthermore, the anti-wrinkle properties of genistein as well as the positive effect of genistein on greasy skin and acne are particularly improved, if genistein is applied to the skin of a patient in the form of a topical cosmetic or pharmaceutical composition of the present invention.

The effect of genistein-containing compositions for the prevention of UV-induced skin aging, reduction of hair loss and even repairing damaged skin is also improved, if genistein is applied in the form of a topical cosmetic or pharmaceutical composition of the present invention. Of course, the topical cosmetic or pharmaceutical compositions of the present invention can be used with excellent results for treating hyperreactive skin and in particular skin disorders such as eczema, acne, herpes virus infections, psoriasis or light dermatosis as well as treating skin inflammation, pruritis, sensitivity or DNA synthesis and repair deficiency.

Furthermore, genistein has an antibacterial activity, and therefore, the present invention also relates to the use of the topical compositions of the present invention as antibacterial agents, e.g. in particular for biocidal applications such as biocidal application to surfaces.

Furthermore, the topical and pharmaceutical compositions of the present invention can contain the genistein in much higher concentrations than the prior art cosmetic and pharmaceutical compositions, because there is no recrystallization in the compositions.

The genistein nanoparticle compositions of the present invention contain genistein and preferably a carrier. The carrier is not specifically restricted and is generally added to facilitate the formation of a spray-dried powder that can be handled more easily. Without the carrier, the spray-dried powder would be very fine, resulting in low yield and high dusting. In a preferred embodiment the carrier also functions as a stabilizer to minimize the flocculation of nanoparticles in aqueous suspensions, in particular, if the stabilizer is e.g. modified starch, cellulose derivatives, gum acacia and milk protein. Generally, the carrier is selected from one or more carbohydrates, one or more proteins or a mixture of carbohydrates and proteins. Preferred carbohydrates are modified starch, sorbitol, maltose, maltodextrin, gum acacia, pectin, alginate, guar gum, xanthan, cellulose derivatives such as carboxymethylcellulose and hydroxypropylmethylcellulose and mixtures thereof. Most preferred are modified starch and mixtures comprising modified starch, and the modified starch is preferably a starch which is hydrophobically modified, so that it can act as a surfactant. An example of such a hydrophobically modified starch is starch sodium octenyl succinate which is e.g. available under the designation "Capsul" from National Starch and Co., New Jersey, USA.

If the carrier comprises a protein, the protein is preferably selected from gelatin, milk protein, soy protein and mixtures thereof. Furthermore, mixtures of one or more carbohydrates as defined above with one or more proteins as defined above can be used, if appropriate.

Preferred carriers which are contained in the genistein nanoparticle compositions of the present invention are carriers which also have the ability to stabilize an aqueous suspension of the genistein. Such carriers generally contain a hydrophobic part and a hydrophilic part such as hydrophobically modified starch, cellulose derivatives such as hydroxypropylmethylcellulose, gum acacia and milk proteins. These carriers/stabilizers are preferred components of the genistein nanoparticle compositions of the present invention.

However, it should be understood that it is not essential for the invention that the carrier also has a stabilizing function on suspensions of the genistein. The genistein nanoparticle compositions of the invention are used in topical, pharmaceutical or cosmetic compositions which might already contain suspension stabilizers (or the formulation process alone is adequate to resuspend the genistein nanoparticles), and therefore, the presence of a suspension stabilizer in the genistein nanoparticle compositions of the invention is not absolutely necessary. However, if the genistein nanoparticle compositions of the invention already contain a carrier which has also suspension stabilizing activity, it might be possible to reduce the amount of suspension stabilizer in the topical cosmetic or pharmaceutical composition which is prepared with the genistein nanoparticle compositions of the invention.

The genistein nanoparticle compositions of the invention are usually prepared as aqueous suspensions containing genistein, optionally a carrier and water. Optionally the aqueous suspensions are then subjected to a suitable drying method such as spray-drying or freeze-drying to eliminate most or all of the water and to obtain a granular or powdery product. According to the present invention both compositions are preferred, the aqueous suspensions containing genistein, water and optionally a carrier and the dry compositions containing genistein and optionally a carrier. Thus, in a preferred embodiment the compositions of the invention consist of genistein, optionally a carrier and optionally water. It should be understood that the term carrier as used therein includes a mixture of several different carriers as defined above.

If the genistein nanoparticle compositions of the present invention are powder compositions or granular compositions, they comprise preferably at least 1 wt.-% of genistein, preferably 20 wt.-% or more, more preferably 50 wt.-% of genistein or more with 90 wt.-% of genistein or more also being preferred. The rest of the genistein nanoparticle compositions is the optional carrier and, depending on the drying process, residual water which is not removed from the genistein nanoparticle composition. Thus, preferably the genistein nanoparticle composition contains 99 wt.-% or less of carrier and, if applicable, residual water, preferably 80 wt.-% or less, more preferably 50 wt.-% or less of carrier and, if applicable, residual water, and 10 wt.-% or less of carrier and, if applicable, residual water is also preferred. Preferably the genistein nanoparticle compositions of the present invention contain at least 1 wt.-% of carrier and, if applicable, residual water, preferably the genistein nanoparticle compositions of the present invention contain 5 wt.-% or more of carrier and, if applicable, residual water. Preferred granular or powder genistein nanoparticle compositions contain genistein in an amount from 1 to 99 wt.-%, from 15 to 95 wt.-%, from 30 to 95 wt.-%, from 50 to 95 wt.-%, from 70 to 95 wt.-%, from 70 to 90 wt.-%, from 90 to 99 wt.-%, from 90 to 95 wt.-%, the rest being carrier and, if applicable, residual water. Of course, compositions not containing a carrier but only genistein and, if applicable, residual water are also preferred. The genistein nanoparticle compositions in the form of a powder can be prepared from the aqueous suspensions described below by a conventional spray drying process or a freeze drying process.

If the genistein nanoparticle composition of the present invention is in the form of an aqueous suspension containing genistein, optionally a carrier and water, the amount of water is not particularly restricted, but generally these aqueous compositions will contain 0.5% or more, preferably 3% or more, preferably 5% or more of genistein and optionally a carrier, more preferably 10% or more, more preferably 20% or more, 30% or more, 40% or more or 50% or more of genistein and optionally carrier, the rest being water, wherein the relative amounts of genistein and carrier are as defined above or below. The minimum amount of water which is present in the aqueous suspensions is the amount necessary to form a suspension. The aqueous suspensions of the invention can be directly obtained from the production process and in this case the amount of solid particles in the suspension and thus also the amount of water in the suspension depends on the equipment which is used for preparing the suspension. If a higher solids content should be provided, it is possible to remove water from the aqueous suspension as required, e.g. by evaporation, preferably at constant temperature. Preferred are aqueous suspensions which are directly obtained by high pressure homogenization or by agitated bead milling (wet grinding) of genistein and optionally a carrier, and such suspensions usually contain 40% or more of water. Aqueous suspensions which contain 50% or more of water, the rest being genistein and optionally a carrier in relative amounts as defined above, are also preferred.

Preferred compositions are also compositions containing genistein in an amount in the range of 10 to 50 wt.-% and carrier in an amount of a ratio of genistein to carrier in the range of 10:1 to 1:10, preferably 10:1 to 1:1 or 1:1 to 1:5 such as about 1:2, the rest of the composition being water, such as compositions containing 25% of genistein, 5% of carrier and 70% of water. Preferred are also compositions containing 10 to 30% of genistein (preferred 15 to 25% of genistein particularly about 20% of genistein), 15 to 40% of carrier (preferred 20 to 30% of carrier, particularly about 25% of carrier) and the rest being water.

An important feature of the genistein nanoparticle compositions of the invention is the particle size of the genistein, which is 3 µm or less, preferably 1 µm or less, such as about 0.5 µm. Preferred ranges of the average particle size of the genistein in the genistein nanoparticle compositions of the invention are 0.05 to 3 µm, more preferred 0.05 to 1 µm, still more preferred 0.05 to 0.5 µm. Furthermore, a particle size of 0.3 to 1.0 µm is preferred. Preferred are also the above ranges with 0.1 instead of 0.05 as lower limit for the average particle size. All particle sizes above are average particle sizes D[4,3], i.e. volume mean diameters or De Brouckere mean diameters. Preferably, the particle size of the genistein particles according to D[3,2] are within the ranges of 0.05 to 0.5, preferably of 0.1 to 0.2, where D[3,2] is the surface mean diameter or the sauter mean diameter. All measurements of particle size referred to in this specification are made by laser diffraction technique using a "Matersizer 2000" of Malvern Instruments Ltd., UK, and further information on the above particle sizes D[4,3] and D[3,2] can e.g. be found in "Basic principles of particle size analytics", Dr. Alan Rawle, Malvern Instruments Limited, Engima Business Part, Grovewood Road, Malvern, Worcestershire, WR14 1XZ, UK and the "Manual of Malvern particle size analyzer".

Applicants do not wish to be bound by theory, and it is not known whether the particles in the carrier containing genistein nanoparticle composition of the present invention contain a mixture of genistein and carrier, which means that genistein and the carrier are present in the same particle, or whether particles of genistein and particles of carrier are independently present in the genistein nanoparticle compositions. It is also possible that the genistein nanoparticle composition contains particles which consist solely of genistein, particles which comprise both genistein and carrier and particles which consist solely of carrier. All these possibilities are included within the present invention, and if the genistein nanoparticle compositions of the present invention comprise particles which contain both genistein and carrier, the above particle size refers to the particle as such comprising both genistein and the carrier.

If nothing else is stated, in this application parts and percentages are per weight and are based on the weight of the composition.

The present invention provides topical compositions, in particular topical cosmetic and pharmaceutical compositions with topical cosmetic compositions being preferred.

The term "cosmetic preparation" or "cosmetic composition" as used in the present application refers to cosmetic compositions as defined under the heading "Kosmetika" in Römpp Lexikon Chemie, 10th edition 1997, Georg Thieme Verlag Stuttgart, New York.

The cosmetic or pharmaceutical compositions of the present invention contain the genistein nanoparticle compositions of the present invention together with cosmetically or pharmaceutically acceptable excipients or diluents. If nothing else is stated, the excipients, additives, diluents, etc. mentioned in the following are suitable for both pharmaceutical and cosmetic compositions.

Preferably, the cosmetic or pharmaceutical compositions of the present invention are topical compositions, such as liquid or solid oil-in-water emulsions, water-in-oil emulsions, multiple emulsions, microemulsions, PET-emulsions, bickering emulsions, hydrogels, alcoholic gels, lipogels, one or multiphase solutions, foams, ointments, plasters, suspensions, shampoos, powders, crèmes, cleanser, soaps and other usual compositions, which can also be applied by pens, as masks or as sprays. Aqueous suspensions are most preferred.

The cosmetic or pharmaceutical compositions of the invention can also contain usual cosmetic or pharmaceutical adjuvants and additives, such as preservatives/antioxidants, fatty substances/oils, water, organic solvents, silicones, thickeners, softeners, emulsifiers, sunscreens, antifoaming agents, moisturizers, fragrances, surfactants, fillers, sequestering agents, anionic, cationic, nonionic or amphoteric polymers or mixtures thereof, propellants, acidifying or basifying agents, dyes, colorants, pigments or nanopigments, e.g. those suited for providing a photoprotective effect by physically blocking out ultraviolet radiation, or any other ingredients usually formulated into cosmetics or medicaments.

An additional amount of antioxidants/preservatives is generally preferred. Based on the invention all known antioxidants usually formulated into cosmetics or medicaments can be used. Especially preferred are antioxidants chosen from the group consisting of amino acids (e.g. glycine, histidine, tyrosine, tryptophan) and their derivatives, imidazole (e.g. urocanic acid) and derivatives, peptides such as D,L-carnosine, D-carnosine, L-carnosine and derivatives (e.g. anserine), carotenoids, carotenes (e.g. α-carotene, β-carotene, lycopene) and derivatives, chlorogenic acid and derivatives, lipoic acid and derivatives (e.g. dihydrolipoic acid), aurothioglucose, propylthiouracil and other thiols (e.g. thioredoxin, glutathione, cysteine, cystine, cystamine and its glycosyl-, N-acetyl-, methyl-, ethyl-, propyl-, amyl-, butyl- and lauryl-, palmitoyl-; oleyl-, γ-linoleyl-, cholesteryl- and glycerylester) and the salts thereof, dilaurylthiodipropionate, distearylthiodipropionate, thiodipropionic acid and its derivatives (ester, ether, peptides, lipids, nucleotides, nucleosides and salts) as well as sulfoximine compounds (such as buthioninsulfoximine, homocysteinesulfoximine, buthioninsulfone, penta-, hexa-, heptathioninsulfoximine) in very low compatible doses (e.g. pmol to μmol/kg), additionally (metal)-chelators (such as α-hydroxyfatty acids, palmic-, phytinic acid, lactoferrin), β-hydroxyacids (such as citric acid, lactic acid, malic acid), huminic acid, gallic acid, gallic extracts, bilirubin, biliverdin, EDTA, EGTA and its derivatives, unsaturated fatty acids and their derivatives (such as γ-linoleic acid, linolic acid, oleic acid), folic acid and its derivatives, ubiquinone and ubiquinol and their derivatives, vitamin C and derivatives (such as ascorbylpalmitate and ascorbyltetraisopalmitate, Mg-ascorbylphosphate, Na-ascorbylphosphate, Na-ascorbylacetate), tocopherol and derivatives (such as vitamin-E-acetate), mixtures of nat. vitamin E, vitamin A and derivatives (vitamin-A-palmitate and -acetate) as well as coniferylbenzoate, rutinic acid and derivatives, α-glycosylrutin, ferulic acid, furfurylideneglucitol, carnosine, butylhydroxytoluene, butylhydroxyanisole, trihydroxybutyrophenone, urea and its derivatives, mannose and derivatives, zinc and derivatives (e.g. ZnO, $ZnSO_4$), selenium and derivatives (e.g. selenomethionin), stilbenes and derivatives (such as stilbenoxide, trans-stilbenoxide) and suitable derivatives (salts, esters, ethers, sugars, nucleotides, nucleosides, peptides and lipids) of the named active ingredients. One or more preservatives/antioxidants may be present in an amount about 0.01 wt.-% to about 10 wt.-% of the total weight of the cosmetic or pharmaceutical topical composition of the present invention. Preferably, one or more preservatives/antioxidants are present in an amount about 0.1 wt.-% to about 1 wt.-%.

Typically topical cosmetic or pharmaceutical formulations also contain surface active ingredients like emulsifiers, solubilizers and the like. An emulsifier enables two or more immiscible components to be combined homogeneously. Moreover, the emulsifier acts to stabilize the composition. Emulsifiers that may be used in the present invention in order to form O/W, W/O, O/W/O or W/O/W emulsions/microemulsions include sorbitan oleate, sorbitan sesquioleate, sorbitan isostearate, sorbitan trioleate, polyglyceryl-3-diisostearate, polyglycerol esters of oleic/isostearic acid, polyglyceryl-6 hexaricinolate, polyglyceryl-4-oleate, polyglyceryl-4 oleate/PEG-8 propylene glycol cocoate, oleamide DEA, TEA myristate, TEA stearate, magnesium stearate, sodium stearate, potassium laurate, potassium ricinoleate, sodium cocoate, sodium tallowate, potassium castorate, sodium oleate, and mixtures thereof. Further suitable emulsifiers are phosphate esters and the salts thereof such as cetyl phosphate (Amphisol® A), diethanolamine cetyl phosphate (Amphisol®), potassium cetyl phosphate (Amphisol® K), sodium glyceryl oleate phosphate, hydrogenated vegetable glyceride phosphates and mixtures thereof. Furthermore, one or more synthetic polymers may be used as an emulsifier. For example, PVP eicosene copolymer, acrylates/$C_{10-30}$ alkyl acrylate crosspolymer, acrylates/steareth-20 methacrylate copolymer, PEG-22/dodecyl glycol copolymer, PEG-45/dodecyl glycol copolymer, and mixtures thereof. The preferred emulsifiers are cetyl phosphate (Amphisol® A), diethanolamine cetyl phosphate (Amphisol®), potassium cetyl phosphate (Amphisol® K), PVP Eicosene copolymer, acrylates/$C_{10-30}$-alkyl acrylate crosspolymer, PEG-20 sorbitan isostearate, sorbitan isostearate, and mixtures thereof. The one or more emulsifiers are present in a total amount about 0.01 wt.-% to about 20 wt.-% of the total weight of the cosmetic or pharmaceutical topical composition of the present invention. Preferably, about 0.1 wt.-% to about 10 wt.-% of emulsifiers is used.

The lipid phase of the topical cosmetic or pharmaceutical compositions can advantageously be chosen from:
mineral oils and mineral waxes;
oils such as triglycerides of caprinic acid or caprylic acid and castor oil;
oils or waxes and other natural or synthetic oils, in a preferred embodiment esters of fatty acids with alcohols e.g. isopropanol, propylene glycol, glycerin or esters of fatty alcohols with carboxylic acids or fatty acids;
alkylbenzoates; and/or
silicone oils such as dimethylpolysiloxane, diethylpolysiloxane, diphenylpolysiloxane, cyclomethicones and mixtures thereof.

Exemplary fatty substances which can be incorporated in the oil phase of the emulsion, microemulsion, oleo gel, hydrodispersion or lipodispersion of the cosmetic or pharmaceutical composition of the present invention are advantageously chosen from esters of saturated and/or unsaturated, linear or branched alkyl carboxylic acids with 3 to 30 carbon atoms, and saturated and/or unsaturated, linear and/or branched alcohols with 3 to 30 carbon atoms as well as esters of aromatic carboxylic acids and of saturated and/or unsaturated, linear or branched alcohols of 3-30 carbon atoms. Such esters can advantageously be selected from octylpalmitate, octylcocoate, octylisostearate, octyldodecylmyristate, cetearylisononanoate, isopropylmyristate, isopropylpalmitate, isopropylstearate, isopropyloleate, n-butylstearate, n-hexyllaureate, n-decyloleate, isooctylstearate, isononylstearate, isononylisononanoate, 2-ethyl hexylpalmitate, 2-ethylhexyllaurate, 2-hexyldecylstearate, 2-octyldodecylpalmitate, stearylheptanoate, oleyloleate, oleylerucate, erucyloleate, erucylerucate, tridecylstearate, tridecyltrimellitate, as well as synthetic, half-synthetic or natural mixtures of such esters e.g. jojoba oil.

Other fatty components suitable for use in the topical cosmetic or pharmaceutical compositions of the present invention include polar oils such as lecithins and fatty acid triglycerides, namely triglycerol esters of saturated and/or unsaturated, straight or branched carboxylic acid with 8 to 24 carbon atoms, preferably of 12 to 18 carbon-atoms whereas the fatty acid triglycerides are preferably chosen from synthetic, half synthetic or natural oils (e.g. cocoglyceride, olive oil, sun flower oil, soybean oil, peanut oil, rape seed oil, sweet almond oil, palm oil, coconut oil, castor oil, hydrogenated castor oil, wheat oil, grape seed oil, macadamia nut oil and others); apolar oils such as linear and/or branched hydrocarbons and waxes e.g. mineral oils, vaseline (petrolatum); paraffins, squalane and squalene, polyolefins, hydrogenated polyisobutenes and isohexadecanes, favored polyolefins are polydecenes; dialkyl ethers such as dicaprylylether; linear or cyclic silicone oils such as preferably cyclomethicones (octamethylcyclotetrasiloxane; cetyldimethicone, hexamethylcyclotrisiloxane, polydimethylsiloxane; poly(methylphenylsiloxane) and mixtures thereof.

Other fatty components which can advantageously be incorporated in topical cosmetic or pharmaceutical compositions of the present invention are isoeikosane; neopentylglycoldiheptanoate; propyleneglycoldicaprylate/dicaprate; caprylic/capric/diglycerylsuccinate; butyleneglycol caprylat/caprat; $C_{12-13}$-alkyllactate; di-$C_{12-13}$ alkyltartrate; triisostearin; dipentaerythrityl hexacaprylat/hexacaprate; propyleneglycolmonoisostearate; tricaprylin; dimethylisosorbid. Especially beneficial is the use of mixtures $C_{12-15}$-alkylbenzoate and 2-ethylhexylisostearate, mixtures $C_{12-15}$-alkylbenzoate and isotridecylisononanoate as well as mixtures of $C_{12-15}$-alkylbenzoate, 2-ethylhexylisostearate and isotridecylisononanoate.

The oily phase of the cosmetic or pharmaceutical compositions of the present invention can also contain natural vegetable or animal waxes such as bee wax, china wax, bumblebee wax and other waxes of insects as well as shea butter and cocoa butter.

A moisturizing agent may be incorporated into a topical cosmetic or pharmaceutical composition of the present invention to maintain hydration or rehydrate the skin. Moisturizers that prevent water from evaporating from the skin by providing a protective coating are called emollients. Additionally an emollient provides a softening or soothing effect on the skin surface and is generally considered safe for topical use. Preferred emollients include mineral oils, lanolin, petrolatum, capric/caprylic triglyceraldehydes, cholesterol, silicones such as dimeticone, cyclometicone, almond oil, jojoba oil, avocado oil, castor oil, sesame oil, sunflower oil, coconut oil and grape seed oil, cocoa butter, olive oil aloe extracts, fatty acids such as oleic and stearic, fatty alcohols such as cetyl and hexadecyl (ENJAY), diisopropyl adipate, hydroxybenzoate esters, benzoic acid esters of $C_{9-15}$-alcohols, isononyl isononanoate, ethers such as polyoxypropylene butyl ethers and polyoxypropylene cetyl ethers, and $C_{12-15}$-alkyl benzoates, and mixtures thereof. The most preferred emollients are hydroxybenzoate esters, aloe vera, $C_{12-15}$-alkyl benzoates, and mixtures thereof. An emollient is present in an amount of about 1 wt.-% to about 20 wt.-% of the total weight of the topical cosmetic or pharmaceutical composition. The preferred amount of emollient is about 2 wt.-% to about 15 wt.-%, and most preferably about 4 wt.-% to about 10 wt.-%.

Moisturizers that bind water, thereby retaining it on the skin surface are called humectants. Suitable humectants can be incorporated into a topical cosmetic or pharmaceutical composition of the present invention such as glycerin, polypropylene glycol, polyethylene glycol, lactic acid, pyrrolidone carboxylic acid, urea, phospholipids, collagen, elastin, ceramides, lecithin sorbitol, PEG-4, and mixtures thereof. Additional suitable moisturizers are polymeric moisturizers of the family of water soluble and/or swellable/and/or with water gelating polysaccharides such as hyaluronic acid, chitosan and/or a fucose rich polysaccharide which is e.g. available as Fucogel®1000 (CAS-Nr. 178463-23-5) by SOLABIA S. One or more humectants are optionally present at about 0.5 wt.-% to about 8 wt.-% in a cosmetic or pharmaceutical topical composition of the present invention, preferably about 1 wt.-% to about 5 wt.-%.

The aqueous phase of the preferred topical cosmetic or pharmaceutical compositions of the present invention can contain the usual cosmetic or pharmaceutical additives such as alcohols, especially lower alcohols, preferably ethanol and/or isopropanol, low diols or polyols and their ethers, preferably propyleneglycol, glycerin, ethyleneglycol, ethyleneglycol monoethyl- or monobutylether, propyleneglycol monomethyl- or -monoethyl- or -monobutylether, diethyleneglycol monomethyl- or monoethylether and analogue products, polymers, foam stabilizers; electrolytes and especially one or more thickeners. However, preferably the cosmetic or pharmaceutical compositions of the present invention are free of ethanol, more preferably they are free of alcohols, and most preferably they are free of organic solvents, since such compounds can cause skin irritation.

Thickeners that may be used in cosmetic or pharmaceutical topical formulations of the present invention to assist in making the consistency of a product suitable include carbomer, siliciumdioxide, magnesium and/or aluminium silicates, beeswax, stearic acid, stearyl alcohol polysaccharides and their derivatives such as xanthan gum, hydroxypropyl cellulose, polyacrylamides, acrylate crosspolymers preferably a carbomer, such as Carbopole® of type 980, 981, 1382, 2984, 5984 alone or mixtures thereof.

Suitable neutralizing agents which may be included in the topical cosmetic or pharmaceutical composition of the present invention to neutralize components such as e.g. an emulsifier or a foam builder/stabilizer include but are not limited to alkali hydroxides such as a sodium and potassium hydroxide; organic bases such as diethanolamine (DEA), triethanolamine (TEA), aminomethyl propanol, and mixtures thereof; amino acids such as arginine and lysine and any combination of any foregoing. The neutralizing agent can be present in an amount of about 0.01 wt.-% to about 8 wt.-% in the cosmetic or pharmaceutical topical composition of the present invention, preferably, 1 wt.-% to about 5 wt.-%.

The addition of electrolytes into the cosmetic or pharmaceutical topical composition of the present invention may be necessary to change the behavior of a hydrophobic emulsifier.

Thus, the emulsions/microemulsions of this invention may contain preferably electrolytes of one or several salts including anions such as chloride, sulfates, carbonate, borate and aluminate, without being limited thereto. Other suitable electrolytes can be on the basis of organic anions such as, but not limited to, lactate, acetate, benzoate, propionate, tartrate and citrate. As cations preferably ammonium, alkylammonium, alkali- or alkaline earth metals, magnesium-, iron- or zinc-ions are selected. Especially preferred salts are potassium and sodium chloride, magnesium sulfate, zinc sulfate and mixtures thereof. Electrolytes can be present in an amount of about 0.01 wt.-% to about 8 wt.-% in the cosmetic or pharmaceutical topical composition of the present invention.

The topical cosmetic or pharmaceutical compositions of the invention can preferably be provided in the form of a lotion, a thickened lotion, a gel, a cream, a milk, an ointment, a powder or a solid tube stick and can be optionally be packaged as an aerosol and can be provided in the form of a mousse, foam or a spray. The cosmetic or pharmaceutical topical compositions according to the invention can also be in the form of a suspension or dispersion in solvents, in particular in water or fatty substances, or alternatively in the form of an emulsion or microemulsion (in particular of O/W or W/O type, O/W/O or W/O/W-type), such as a cream or a milk, a vesicular dispersion, in the form of an ointment, a gel, a solid tube stick or an aerosol mousse. The emulsions can also contain anionic, nonionic, cationic or amphoteric surfactants.

The topical application of the cosmetic or pharmaceutical topical compositions of the present invention is preferably at least once per day, e.g. twice or triple times a day or more. The amount of the topical cosmetic or pharmaceutical composition, which is to be applied to the skin, depends on the concentration of the genistein and optionally other active ingredients in the compositions and the desired cosmetic or pharmaceutical effect. For example, application can be such that a crème is applied to the skin: A crème is usually applied in an amount of 2 mg crème/cm$^2$ skin. The amount of the cosmetic or pharmaceutical topical composition which is applied to the skin is, however, not critical, and if with a certain amount of applied cosmetic or pharmaceutical topical composition the desired effect cannot be achieved, a higher concentration of the genistein can be used e.g. by applying more of the cosmetic or pharmaceutical composition or by applying cosmetic or pharmaceutical compositions which contain more genistein.

Additionally the cosmetic and pharmaceutical topical composition of the present invention may contain UV-A and UV-B filters. Examples of UV-B or broad spectrum screening agents, i.e. substances having absorption maximums between about 290 and 340 nm, which are preferred for combination with the cosmetic or pharmaceutical topical compositions of the present invention, are the following organic and inorganic compounds:

Acrylates such as 2-ethylhexyl 2-cyano-3,3-diphenylacrylate (octocrylene, PARSOL® 340), ethyl 2-cyano-3,3-diphenylacrylate and the like;
  Camphor derivatives such as 4-methyl benzylidene camphor (PARSOL® 5000), 3-benzylidene camphor, camphor benzalkonium methosulfate, polyacrylamidomethyl benzylidene camphor, sulfo benzylidene camphor, sulfomethyl benzylidene camphor, therephthalidene dicamphor sulfonic acid and the like;
  Cinnamate derivatives such as octyl methoxycinnamate (PARSOL® MCX), ethoxyethyl methoxycinnamate, diethanolamine methoxycinnamate (PARSOL® Hydro), isoamyl methoxycinnamate and the like as well as cinnamic acid derivatives bond to siloxanes;

p-aminobenzoic acid derivatives, such as p-aminobenzoic acid, 2-ethylhexyl p-dimethylaminobenzoate, N-oxypropylenated ethyl p-aminobenzoate, glyceryl p-aminobenzoate, Benzophenones such as benzophenone-3, benzophenone-4,2,2',4,4'-tetrahydroxy-benzophenone, 2,2'-dihydroxy-4,4'-dimethoxybenzophenone and the like;

Esters of Benzalmalonic acid such as di-(2-ethylhexyl) 4-methoxybenzalmalonate;

Esters of 2-(4-ethoxy-anilinomethylene)propanedioic acid such as 2-(4-ethoxy anilinomethylene)propanedioic acid diethyl ester as described in the European Patent Publication EP 0895 776;

Organosiloxane compounds containing benzmalonate groups as described in the European Patent Publications EP 0358584 B1, EP 0538431 B1 and EP 0709080 A1, in particular Parsol SLX;

Drometrizole trisiloxane (Mexoryl XL);

Pigments such as microparticulated TiO$_2$, and the like. The term "microparticulated" refers to a particle size from about 5 nm to about 200 nm, particularly from about 15 nm to about 100 nm. The TiO$_2$ particles may also be coated by metal oxides such as e.g. aluminium or zirconium oxides or by organic coatings such as e.g. polyols, methicone, aluminium stearate, alkyl silane. Such coatings are well known in the art.

Imidazole derivatives such as e.g. 2-phenyl benzimidazole sulfonic acid and its salts (PARSOL®HS). Salts of 2-phenyl benzimidazole sulfonic acid are e.g. alkali salts such as sodium- or potassium salts, ammonium salts, morpholine salts and salts of primary, sec. and tert. amines like monoethanolamine salts, diethanolamine salts and the like.

Salicylate derivatives such as isopropylbenzyl salicylate, benzyl salicylate, butyl salicylate, octyl salicylate (NEO HELIOPAN OS), isooctyl salicylate or homomethyl salicylate (homosalate, HELIOPAN) and the like.

Triazine derivatives such as octyl triazone (UVINUL T-150), dioctyl butamido triazone (UVASORB HEB), bis ethoxyphenol methoxyphenyl triazine (Tinosorb S) and the like.

Examples of broad spectrum or UV A screening agents i.e. substances having absorption maximums between about 320 and 400 nm, which are preferred for the cosmetic or pharmaceutical topical compositions of the present invention are the following organic and inorganic compounds:

Dibenzoylmethane derivatives such as 4-tert. butyl-4'-methoxydibenzoyl-methane (PARSOL® 1789), dimethoxydibenzoylmethane, isopropyldibenzoylmethane and the like;

Benzotriazole derivatives such as 2,2'-methylene-bis-(6-(2H-benzotriazole-2-yl)-4-(1,1,3,3,-tetramethylbutyl)-phenol (TINOSORB M) and the like;

Phenylene-1,4-bis-benzimidazolsulfonic acids or salts such as 2,2-(1,4-phenylene)bis-(1H-benzimidazol-4,6-disulfonic acid) (Neoheliopan AP);

Amino substituted hydroxybenzophenones such as 2-(4-Diethylamino-2-hydroxy-benzoyl)-benzoic acid hexylester as described in the European Patent Publication EP 1046391;

Pigments such as microparticulated ZnO or TiO$_2$ and the like. The term "microparticulated" refers to a particle size from about 5 nm to about 200 nm, particularly from about 15 nm to about 100 nm. The particles may also be coated by other metal oxides such as e.g. aluminium or zirconium oxides or by organic coatings such as e.g.

polyols, methicone, aluminium stearate, alkyl silane. Such coatings are well known in the art.

As dibenzoylmethane derivatives have limited photostability it may be desirable to photostabilize these UV-A screening agents. Thus, the term "conventional UV-A screening agent" also refers to dibenzoylmethane derivatives such as e.g. PARSOL® 1789 stabilized by, e.g.,

- 3,3-Diphenylacrylate derivatives as described in the European Patent Publications EP-A 0 514 491 and EP-A 0 780 119;
- Benzylidene camphor derivatives as described in the U.S. Pat. No. 5,605,680;
- Organosiloxanes containing benzmalonate groups as described in the European Patent Publications EP-A 0358584, EP-A 0538431 and EP-A 0709080, in particular Parsol SLX.

A good overview of UV-A- and UV-B-filters which can be added to the compositions of the present invention can also be found in DE-A 103 27 432. All UV-filter compounds disclosed in this document are also useful as components for the compositions of the present invention and are included herein by reference.

The topical cosmetic and pharmaceutical compositions of the present invention preferably comprise more than 0.01%, preferably 0.1% or less, more preferably 0.2% or more of the nanoparticles of genistein and optionally a carrier. However, the effect which is achieved by incorporating the genistein nanoparticle compositions into the topical cosmetic and pharmaceutical compositions is most impressive in pharmaceutical and cosmetic compositions containing 0.3% or more of genistein, because at these high concentrations the topical pharmaceutical and cosmetic compositions of the present invention have a particularly low increase in the particle size of the genistein nanoparticles during storage (and sometimes there is even a decrease). The effect at such high concentrations is much more pronounced than at lower concentrations of less than 0.3%, which is particularly surprising and advantageous, because it allows the provision of cosmetic and pharmaceutical compositions having very high concentrations of genistein, which could not be obtained using prior art genistein compositions. Therefore, the cosmetic and pharmaceutical compositions of the invention will contain the nanoparticles containing genistein and optionally a carrier in a concentration of preferably 0.3% or more, more preferably 0.5% or more. The following ranges of nanoparticles of genistein and optionally carrier are also preferred: 0.3% to 3%, 0.3% to 2%, 0.3% to 1% and the above ranges, where the lower limit is 0.4 or 0.5% instead of 0.3%.

Regarding the kind of the topical cosmetic and pharmaceutical composition and the preparation of the topical cosmetic and pharmaceutical preparations as well as for further suitable additives, it can be referred to the pertinent literature, e.g. to Novak G. A., Die kosmetischen Präparate—Band 2, Die kosmetischen Präparate—Rezeptur, Rohstoffe, wissenschaftliche Grundlagen (Verlag für Chem. Industrie H. Ziolkowski KG, Augsburg).

The composition can also contain one or more additional pharmaceutically or cosmetically active ingredients, in particular for preventing or reducing acne, wrinkles, lines, atrophy, inflammation, as well as topical anesthetics, artificial tanning agents and accelerators, antimicrobial agents, and antifungal agents and sunscreen additives.

Examples are peptides (e.g., Matrixyl™ [pentapeptide derivative]), glycerol, urea, guanidine (e.g., amino guanidine); vitamins and derivatives thereof such as ascorbic acid, vitamin A (e.g., retinoid derivatives such as retinyl palmitate or retinyl propionate), vitamin E (e.g., tocopherol acetate), vitamin $B_3$ (e.g., niacinamide) and vitamin $B_5$ (e.g., panthenol) and the like and mixtures thereof, wax-based synthetic peptides (e.g., octyl palmitate and tribehenin and sorbitan isostearate and palmitoyl-oligopeptide), anti-acne medicaments (resorcinol, salicylic acid, and the like); anti-oxidants (e.g., phytosterols, lipoic acid); flavonoids (e.g., isoflavones, phytoestrogens); skin soothing and healing agents such as aloe vera extract, allantoin and the like; chelators and sequestrants; and agents suitable for aesthetic purposes such as essential oils, fragrances, skin sensates, opacifiers, aromatic compounds (e.g., clove oil, menthol, camphor, eucalyptus oil, and eugenol), desquamatory actives, anti-acne actives, vitamin $B_3$ compounds, anti-oxidants, peptides, hydroxy acids, radical scavengers, chelators, farnesol, anti-inflammatory agents, topical anesthetics, tanning actives, skin-lightening agents, anti-cellulites agents, flavonoids, antimicrobial actives, and antifungal actives, in particular bisabolol, alkyldiols such as 1,2-pentanediol, hexanediol or 1,2-octanediol, vitamins, panthenol, phytol, phytanetriol, ceramides and pseudoceramides, amino acids and bioactive peptides, protein hydrolysates, AHA acids, polyunsaturated fatty acids, plant extracts, DNA or RNA and their fragmentation products or carbohydrates, biotin, conjugated fatty acids, carnitin, vitamin E, A, C, B3, B6, B12, oligopeptides, carnosine, biochinonen, phytofluen, phytoen, folic acid, and their corresponding derivatives.

The genistein nanoparticle compositions of the present invention are preferably obtained by fragmentation of genistein crystals and optionally the carrier in a high pressure homogenizer. The genistein nanoparticle compositions of the present invention are more preferably obtained by milling genistein (in particular-genistein crystals) and optionally carrier in an agitated bead mill. The fragmentation and milling is usually carried out with an aqueous suspension.

Suitable homogenizers are known in the prior art and commercially available and for example it can be referred to DeBEE 2000 high pressure homogenizer of B.E.E. International Ltd., Migdal Haemek, Israel. The homogenizer is preferably operated at a pressure from 500 bar to 4000 bar, more preferably at a pressure from 500 bar to 3000 bar, most preferably at a pressure from 500 bar to 2000 bar. Preferably, the homogenizer is equipped with a nozzle system as disclosed in EP-A 1 008 380.

Preferably the genistein and the carrier are cycled through the high pressure homogenizer 1 to 200 times, more preferably 5 to 100 times, such as 5 to 30 times. The required number of cycles can easily be found by some routine experiments.

In a particularly preferred embodiment first the genistein without the carrier is subjected to a homogenization in a high pressure homogenizer, for example for 5 to 100 times, such as 5 to 30 times, then a solution of the carrier is added and homogenization is continued for example for further 1 to 50, such as 1 to 10 cycles. If necessary, the number of cycles can be increased.

It is believed that during homogenization the genistein crystals are fragmented mostly by cavitation and shearing created in the high pressure process, and the aqueous nanosuspension which is processed can have a solid content of up to 50% or even more. The aqueous nanosuspension can be used as such for preparing the pharmaceutical or cosmetic compositions of the present invention or it can first be subjected to a drying step in order to obtain a powder or granular composition consisting essentially of genistein, optionally the carrier and eventually residual water which is not removed by the drying process. The drying can be done by usual processes such as spray-drying or freeze-drying.

The genistein nanoparticle compositions of the present invention are most preferably obtained by fragmentation in an agitated bead mill by a wet grinding process. Suitable wet grinding mills are known in the prior art and commercially available and for example it can be referred to Netzsch LMZ 4 wet grinding mill of NETZSCH-Feinmahltechnik GmbH, Sedanstraße 70, 95100 Selb, Germany. Preferably the genistein and optionally the carrier are cycled through the agitated bead mill 1-50 times, more preferably 3-40 times, more preferably 5-30 times and most preferably 8-25 times.

The grinding media can consist e.g. essentially of $Al_2O_3$, $Si_3N_4$, $TiO_2$, WC (tungsten carbide) or of $ZrO_2$ or a combination of those compounds. Most preferably $ZrO_2$-type grinding media like $ZrO_2,Y_2O_3$ stabilized are used.

The aqueous nanosuspension which is processed can have a solids content of up to 25% or even more.

In a preferred embodiment of the invention the water is removed as much as possible by choosing suitable drying conditions, and the water content is lower than e.g. 10%.

The following examples are illustrative only but are not intended to limit the scope of the invention.

EXAMPLE 1

A starch sodium octenyl succinate solution (46%) was prepared by dissolving starch sodium octenyl succinate (490 g) available at the National Starch and Chemical Company, New Jersey, US under the product name Capsul, which had a moisture content of 8%, in 80° C. deionized water (490 g).

Genistein powder (20 g) was mixed with the starch sodium octenyl succinate solution (391.4 g) and deionized water (390 g) and passed through a high pressure homogenizer equipped with a 130-micron nozzle; DeBEE 2000, B.E.E. International Ltd., Israel, which had about 200 g of water in the pipeline, at a homogenization pressure of 1500 bar. The back pressure was set at 120 bar during homogenization. The genistein suspension after the nozzle was cooled to about 20 to 30° C. with a heat exchanger. The suspension, with a solid content of about 20%, was cycled through the homogenizer 42 times until the desired particle size was reached. The genistein particle size was determined by laser diffraction technique (Mastersizer 2000, Malvern Instruments Ltd., UK) and the results, calculated based on the refractive index of 1.469, are shown below in Table I.

TABLE I

Particle size measurements of genistein

| | Genistein particle size before homogenization | Genistein particle size after homogenization (42 passes) |
|---|---|---|
| D (v, 0.1) | 17.1 microns | 0.07 microns |
| D (v, 0.5) | 41.9 microns | 0.17 microns |
| D (v, 0.9) | 91.0 microns | 3.65 microns |
| Average particle size D[4, 3]: | 48.5 microns | 0.97 microns |
| Average particle size D[3, 2]: | 23.1 microns | 0.15 microns |

The homogenized genistein suspension was dried with a Niro spray dryer (GEA Niro A/S, Denmark) with a nozzle pressure of 4 bar. The inlet temperature was about 200° C. and outlet temperature was about 80° C. The spray-dry powder contained approximate 9.4% genistein with a moisture content of 5.87%. The genistein particle size was determined by re-dispersing the spray-dry powder in water and measured by the laser diffraction technique and the results are shown in Table II.

TABLE II

Particle size measurements of Spray-dried genistein form

| | Genistein particle size after homogenization (42 passes) and spray-drying |
|---|---|
| D (v, 0.1) | 0.07 microns |
| D (v, 0.5) | 0.16 microns |
| D (v, 0.9) | 2.86 microns |
| Average particle size D[4, 3] | 0.83 microns |
| Average particle size D[3, 2] | 0.14 microns |

EXAMPLE 2

Genistein powder (30 g) was mixed with deionized water (370 g) and passed through a high-pressure homogenizer (equipped with a 130-micron nozzle; DeBEE 2000, BEE International, Israel), which had about 200 g of water in the pipeline, at a homogenization pressure of 1500 bar. The back pressure was set at 120 bar during homogenization. The genistein suspension after the nozzle was cooled to about 20 to 30° C. with a heat exchanger. The suspension, with a solid content of about 5%, was cycled through the homogenizer 40 times until the desired particle size was reached. The genistein particle size was determined by laser diffraction technique (Mastersizer 2000, Malvern Instruments Ltd., UK), and the results, calculated based on the refractive index of 1.469, are shown below in Table III.

TABLE III

Particle size measurements of genistein

| | Genistein particle size before homogenization | Genistein particle size after homogenization (40 passes) |
|---|---|---|
| D (v, 0.1) | 17.1 microns | 0.07 microns |
| D (v, 0.5) | 41.9 microns | 0.16 microns |
| D (v, 0.9) | 91.0 microns | 2.42 microns |
| Average particle size D[4, 3] | 48.5 microns | 0.76 microns |
| Average particle size D[3, 2] | 23.1 microns | 0.14 microns |

A starch sodium octenyl succinate solution (46%) was prepared by dissolving starch sodium octenyl succinate (490 g), which had a moisture content of 8%, in 80° C. deionized water (490 g). A portion of the starch sodium octenyl succinate solution (65 g) was added to the homogenized genistein suspension in the feed funnel at the end of the 40th pass without stopping the homogenization process, and the mixture (approx. 9% solid) was passed through the high pressure homogenizer twice. The genistein particle size was determined by laser diffraction technique (Mastersizer 2000, Malvern Instruments Ltd., UK), and the results are shown below in Table IV.

TABLE IV

Particle size measurements of genistein

| | Genistein particle size after homogenization (42 passes) |
|---|---|
| D (v, 0.1) | 0.07 microns |
| D (v, 0.5) | 0.16 microns |
| D (v, 0.9) | 0.93 microns |
| Average particle size D[4, 3] | 0.41 microns |
| Average particle size D[3, 2] | 0.14 microns |

The homogenized genistein suspension was dried with a Niro spray dryer (GEA Niro A/S, Denmark) with a nozzle pressure of 4 bar. The inlet temperature was about 200° C. and outlet temperature was about 80° C. The spray-dry powder contained approximately 48.5% genistein with a moisture content of 3.24%. The genistein particle size was determined by re-dispersing the spray-dry powder in water and measured by the laser diffraction technique. The results are shown in Table V.

TABLE V

Particle size measurements of Spray-dried genistein form

| | Genistein particle size after homogenization (42 passes) and spray-drying |
|---|---|
| D (v, 0.1) | 0.07 microns |
| D (v, 0.5) | 0.15 microns |
| D (v, 0.9) | 1.14 microns |
| Average particle size D[4, 3] | 0.55 microns |
| Average particle size D[3, 2] | 0.14 microns |

EXAMPLE 3

Genistein powder (36 g) was mixed with deionized water (364 g) and passed through a high-pressure homogenizer (equipped with a 130-micron nozzle; DeBEE 2000, BEE International, Israel), which had about 200 g of water in the pipeline, at a homogenization pressure of 1500 bar. The back pressure was set at 120 bar during homogenization. The genistein suspension after the nozzle was cooled to about 20 to 30° C. with a heat exchanger. The suspension, with a solid content of about 6%, was cycled through the homogenizer 40 times until the desired particle size was reached. The genistein particle size was determined by laser diffraction technique (Mastersizer 2000, Malvern Instruments Ltd., UK), and the results, calculated based on the refractive index of 1.469, are shown below in Table VI.

TABLE VI

Particle size measurements of genistein

| | Genistein particle size before homogenization | Genistein particle size after homogenization (40 passes) |
|---|---|---|
| D (v, 0.1) | 17.1 microns | 0.07 microns |
| D (v, 0.5) | 41.9 microns | 0.16 microns |
| D (v, 0.9) | 91.0 microns | 2.00 microns |
| Average particle size D[4, 3] | 48.5 microns | 0.76 microns |
| Average particle size D[3, 2] | 23.1 microns | 0.14 microns |

A starch sodium octenyl succinate solution (46%) was prepared by dissolving starch sodium octenyl succinate (490 g), which had a moisture content of 8%, in 80° C. deionized water (490 g). A portion of the starch sodium octenyl succinate solution (19.5 g) was added to the homogenized genistein suspension in the feed funnel at the end of the 40th pass without stopping the homogenization process, and the mixture (approx. 7.3% solid) was passed through the high pressure homogenizer twice. The genistein particle size was determined by laser diffraction technique (Mastersizer 2000, Malvern Instruments Ltd., UK), and the results are shown below in Table VII.

TABLE VII

Particle size measurements of genistein

| | Genistein particle size after homogenization (42 passes) |
|---|---|
| D (v, 0.1) | 0.07 microns |
| D (v, 0.5) | 0.16 microns |
| D (v, 0.9) | 0.91 microns |
| Average particle size D[4, 3] | 0.40 microns |
| Average particle size D[3, 2] | 0.14 microns |

The homogenized genistein suspension was dried with a Niro spray-dryer (GEA Niro A/S, Denmark) with a nozzle pressure of 4 bar. The inlet temperature was about 200° C. and outlet temperature was about 80° C. The spray-dry powder contained approximately 78.2% genistein with a moisture content of 2.31%. The genistein particle size was determined by re-dispersing the spray-dry powder in water and measured by the laser diffraction technique. The results are shown below in Table VIII.

TABLE VIII

Particle size measurements of Spray-dried genistein form

| | Genistein particle size after homogenization (42 passes) and spray-drying |
|---|---|
| D (v, 0.1) | 0.07 microns |
| D (v, 0.5) | 0.16 microns |
| D (v, 0.9) | 0.97 microns |
| Average particle size D[4, 3] | 0.43 microns |
| Average particle size D[2, 3] | 0.14 microns |

EXAMPLE 4

Genistein powder (120 g) was mixed with deionized water (280 g) and passed through a high-pressure homogenizer (equipped with a 180-micron nozzle; DeBEE 2000, BEE International, Israel), which had about 200 g of water in the pipeline, at a homogenization pressure of 700 bar. The back pressure was set at 120 bar during homogenization. The genistein suspension after the nozzle was cooled to about 20 to 30° C. with a heat exchanger. The suspension, with a solid content of about 20%, was cycled through the homogenizer 20 times until the desired particle size was reached. The genistein particle size was determined by laser diffraction technique (Mastersizer 2000, Malvern Instruments Ltd., UK), and the results, calculated based on the refractive index of 1.469, are shown below in Table IX.

TABLE IX

Particle size measurements of genistein

| | Genistein particle size before homogenization | Genistein particle size after homogenization (20 passes) |
|---|---|---|
| D (v, 0.1) | 17.1 microns | 0.07 microns |
| D (v, 0.5) | 41.9 microns | 0.15 microns |
| D (v, 0.9) | 91.0 microns | 2.62 microns |
| Average particle size D[4, 3] | 48.5 microns | 0.83 microns |
| Average particle size D[3, 2] | 23.1 microns | 0.13 microns |

EXAMPLE 5

Genistein powder (36 g) was mixed with deionized water (364 g) and passed through a high-pressure homogenizer (equipped with a 130-micron nozzle; DeBEE 2000, BEE International, Israel), which had about 200 g of water in the pipeline, at a homogenization pressure of 1500 bar. The back pressure was set at 120 bar during homogenization. The genistein suspension after the nozzle was cooled to about 20 to 30° C. with a heat exchanger. The suspension, with a solid content of about 6%, was cycled through the homogenizer 40 times until the desired particle size was reached. The genistein particle size was determined by laser diffraction technique (Mastersizer 2000, Malvern Instruments Ltd., UK), and the results, calculated based on the refractive index of 1.469, are shown below in Table X.

TABLE X

Particle size measurements of genistein

|  | Genistein particle size before homogenization | Genistein particle size after homogenization (20 passes) |
| --- | --- | --- |
| D (v, 0.1) | 17.8 microns | 0.07 microns |
| D (v, 0.5) | 41.4 microns | 0.16 microns |
| D (v, 0.9) | 90.2 microns | 0.92 microns |
| Average particle size D[4, 3] | 48.5 microns | 0.42 microns |
| Average particle size D[2, 3] | 23.1 microns | 0.14 microns |

A maltodextrin solution (45%; 52 g) was prepared by dissolving maltodextrin (25 g), which had a moisture content of 6.18%, in deionized water (27 g). A portion of the maltodextrin solution (19.5 g) was added to the homogenized genistein suspension in the feed funnel at the end of the 40th pass without stopping the homogenization process, and the mixture (approx. 7.3% solid) was passed through the high pressure homogenizer twice more. The genistein particle size was determined by laser diffraction technique (Mastersizer 2000, Malvern Instruments Ltd., UK), and the results are shown below in Table XI.

TABLE XI

Particle size measurements of Spray-dried genistein form

|  | Genistein particle size after homogenization (42 passes) and spray-drying |
| --- | --- |
| D (v, 0.1) | 0.07 microns |
| D (v, 0.5) | 0.16 microns |
| D (v, 0.9) | 0.93 microns |
| Average particle size D[4, 3] | 0.41 microns |
| Average particle size D[3, 2] | 0.14 microns |

The homogenized genistein suspension was dried with a Niro spray-dryer (GEA Niro A/S, Denmark) with a nozzle pressure of 4 bar. The inlet temperature was about 200° C. and outlet temperature was about 80° C. The spray-dry powder contained approximately 78.2% genistein. The genistein particle size was determined by re-dispersing the spray-dry powder in water and measured by the laser diffraction technique. The results are shown below in Table XII.

TABLE XII

Particle size measurements of Spray-dried genistein form

|  | Genistein particle size after homogenization (42 passes) and spray-drying |
| --- | --- |
| D (v, 0.1) | 0.07 microns |
| D (v, 0.5) | 0.15 microns |
| D (v, 0.9) | 0.93 microns |
| Average particle size D[4, 3] | 0.41 microns |
| Average particle size D[3, 2] | 0.13 microns |

EXAMPLE 6

A starch sodium octenyl succinate solution (30%) was prepared by dissolving Capsul (2.8 kg; National Starch and Chemical Company, New Jersey, US), which had a moisture content of 8%, in 70° C. deionized water (5.7 kg).

Genistein powder (3.0 kg) was mixed with the starch sodium octenyl succinate solution (8.5 kg) and deionized water (9.0 kg) and passed through an agitated bead mill (Netzsch type LMZ 4; Netzsch GmbH & Co. Holding KG, Selb, Germany) rotating with 1150 Upm using 0.4 mm $ZrO_2$-type grinding media, consisting of $ZrO_2$ stabilized with $Y_2O_3$. The genistein suspension after the agitated bead mill was cooled to 40-45° C. with a heat exchanger. The suspension with a solid content of about 27% was cycled through the agitated bead mill for 2 hours (11 cycles over the mill) until the desired particle size was reached.

The genistein particle size was determined by laser diffraction technique (Mastersizer 2000, Malvern Instruments Ltd., UK) and the results, calculated based on the refractive index of 1.469, are shown below in Table XIII.

TABLE XIII

Particle size measurements of genistein

|  | Genistein particle size before homogenization | Genistein particle size after homogenization (11 passages) |
| --- | --- | --- |
| D (v, 0.1) | 17.8 microns | 0.07 microns |
| D (v, 0.5) | 41.4 microns | 0.16 microns |
| D (v, 0.9) | 90.2 microns | 0.45 microns |
| Average particle size D[4, 3]: | 48.5 microns | 0.23 microns |

The homogenized genistein suspension can be spray used for the target application field or can be spray dried using the procedure described in example 2.

EXAMPLE 7

Genistein powder (6 kg) is milled in a Jet mill by a dry grinding process. Suitable mill: Alpine 100 AFG by Hosokawa Alpine company using a jet pressure of 5.0 bar and speed of the sifter wheel of 20.000 Upm. This genistein is used in the "swing" test shown in FIG. 7 for comparative reasons.

A starch sodium octenyl succinate solution (48%) was prepared by dissolving starch sodium octenyl succinate (6.0 kg; National Starch and Chemical Company, New Jersey, US), which had a moisture content of 8%, in 70° C. deionized water (6.1 kg).

Figure 8A:
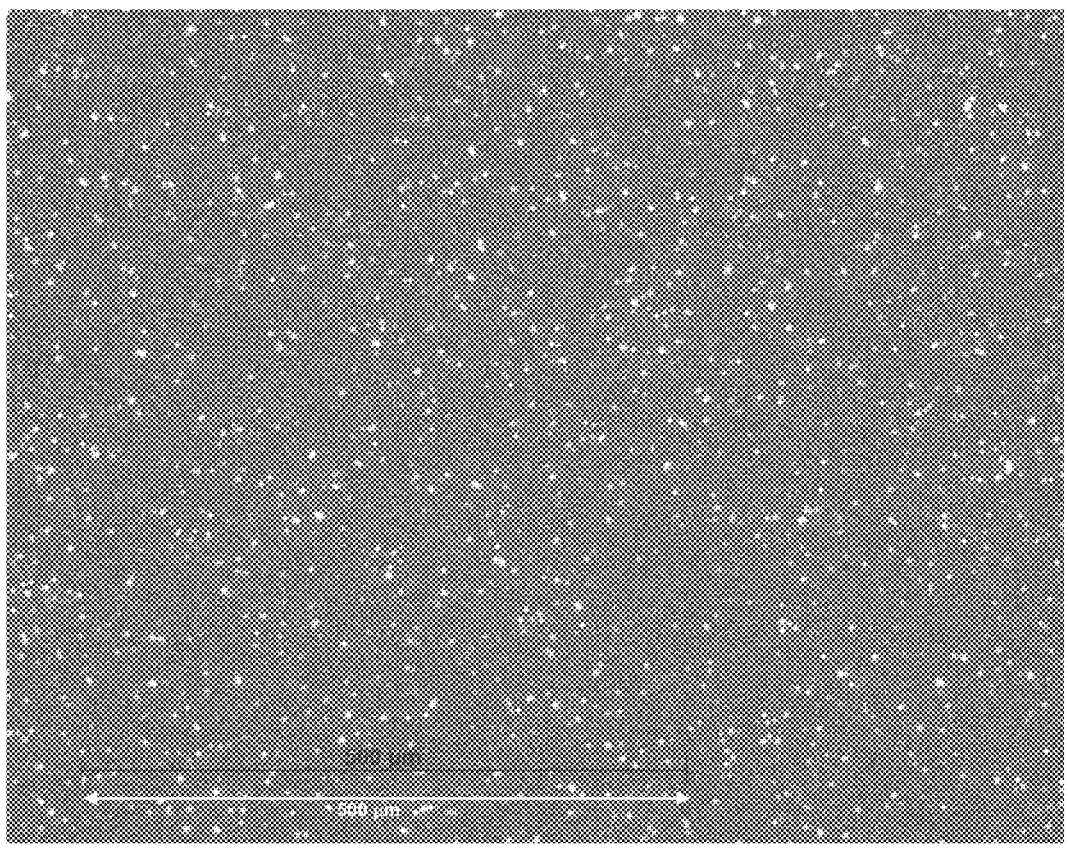
FIGS. 8(a)-8(c) show the final product compositions of example 7 at concentrations of 0.3%, 0.5% and 1.0%.
Figure 8B:
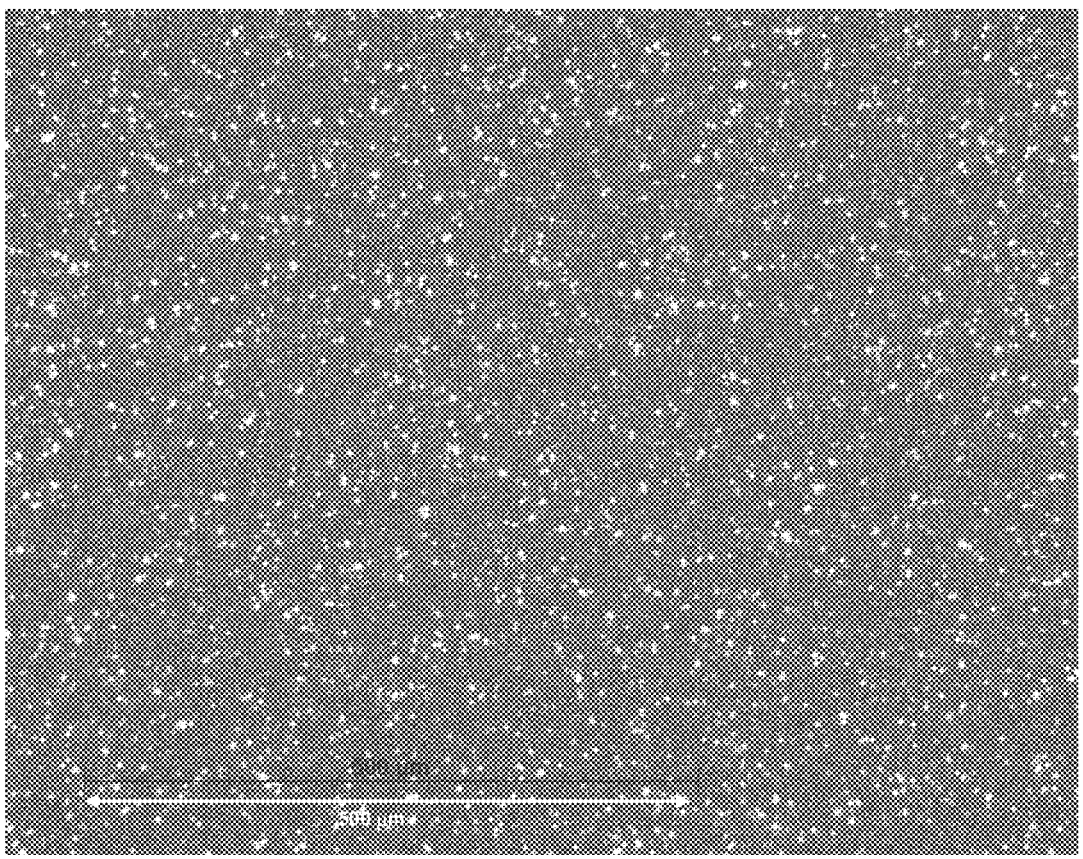
Figure 8C:
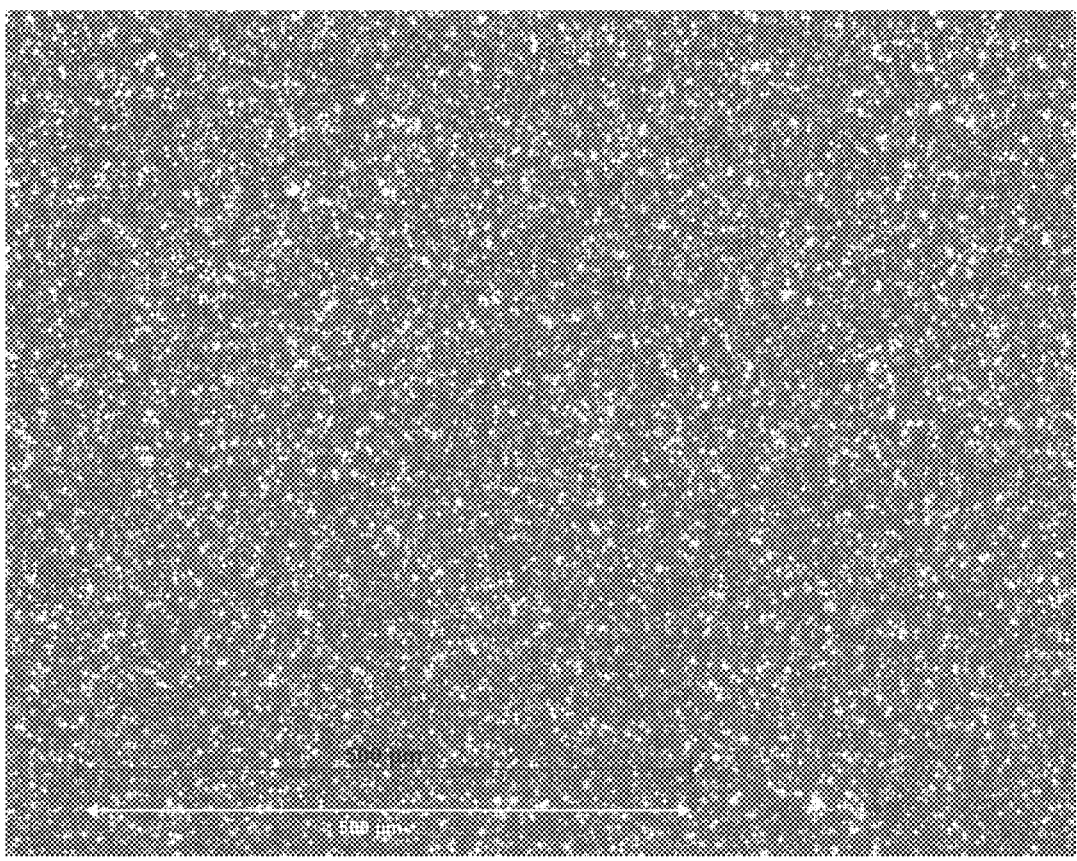

The milled genistein powder (6.0 kg) was mixed with the starch sodium octenyl succinate solution (12.1 kg) and deionized water (24 kg) and passed through a high pressure homogenizer equipped with a mixing device as described in EP 1 008 380 A2 at a homogenization pressure of 700 bar. The genistein suspension after the nozzle was cooled to about 20 to 30° C. with a heat exchanger. The suspension, with a solid content of about 20%, was cycled through the homogenizer 12 times until the desired particle size was reached (final genistein). As illustrated by FIG. 8. The genistein particle size was determined by laser diffraction technique (Mastersizer 2000, Malvern Instruments Ltd., UK) and the results, calculated based on the refractive index of 1.469, are shown below in Table XIV.

TABLE XIV

Particle size measurements of genistein

|  | Genistein particle size before milling and homogenization | Genistein particle size after milling and homgenization |
|---|---|---|
| D (v, 0.1) | 17.8 microns | 0.07 microns |
| D (v, 0.5) | 41.4 microns | 0.18 microns |
| D (v, 0.9) | 90.2 microns | 1.38 microns |
| Average particle size D[4, 3]: | 48.5 microns | 0.53 microns |

The genistein after homogenization was also used in the "swing" test, and the result is shown in FIG. 8.

The homogenized dispersion was spray dried with a Multi Stage Spray dryer with a nozzle pressure of at about 40 bar. The inlet temperature was about 160° C., the outlet temperature was about 80° C. and the inlet air temperature of the internal fluid bed was about 50° C. The genistein particle size was determined by laser diffraction technique (Mastersizer 2000, Malvern Instruments Ltd., UK) and the results, calculated based on the refractive index of 1.469, are shown below in Table XV.

TABLE XV

Particle size measurements of genistein

|  | Genistein particle size before milling and homogenization | Genistein particle size after milling, homgenization and spray drying |
|---|---|---|
| D (v, 0.1) | 17.8 microns | 0.08 microns |
| D (v, 0.5) | 41.4 microns | 0.19 microns |
| D (v, 0.9) | 90.2 microns | 1.84 microns |
| Average particle size D[4, 3]: | 48.5 microns | 0.65 microns |

EXAMPLE 8

O/W emulsions with different genistein forms

| Ingredients | #1 % (w/w) | #2 % (w/w) |
|---|---|---|
| Glyceryl Myristate | 5.00 | 4.00 |
| Cetyl Alcohol | 2.00 | 2.00 |
| Steareth-2 | 2.00 | 2.00 |
| Steareth-21 | 2.00 | 2.00 |
| Isopropyl Mysistate | 10.00 | 5.00 |
| Caprylic/Capric Triglyceride |  | 8.00 |
| BHT | 0.05 | 0.05 |
| Dimethicone | — | 2.00 |
| Phenoxyethanol & Methylparaben & Ethylparaben & Butylparaben & Propylparaben & Isobutylparaben | 0.80 | 0.80 |
| Aqueous suspension of genistein nanoparticles (contains 5.5% genistein, approx. 0.4 microns) | 5.00 | — |
| Genistein (crystalline, approx. 12 microns) | — | 0.10 |
| Water | Ad. 100 | Ad. 100 |
| Polysorbate 20 |  | 1.00 |
| Propylene Glycol | 5.00 | 4.00 |
| Ethoxydiglycol | 8.00 | 10.00 |
| Polyacrylamide & C13-14 Isoparaffin & Laureth-7 | 2.00 | 1.00 |
| Triethanol Amine (10%) | 0.33 | 0.29 |
| Disodium EDETA | 0.10 | 0.10 |

Figure 2:
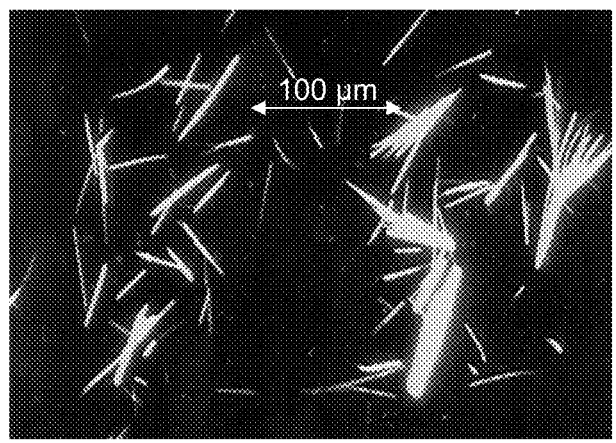

The advantage of using the genistein form consisting of nanoparticles versus the conventional crystalline form in typical cosmetic formulations is illustrated by FIG. 1 and FIG. 2. Cosmetic formulations containing active ingredients should be stable upon storage at different temperatures for at least one year at room temperature. One important parameter monitored in a stability watch is the appearance of the cosmetic formulation under a microscope. Cosmetic formulations containing difficult to solubilize active ingredients will very often develop crystals upon storage, sometimes just within a few days. This phenomenon is even more pronounced by observing formulations which were stored at 5° C. There are many drawbacks with formulations which have developed such large crystals as illustrated in FIG. 2, which shows a microscopical examination of formulation #2 with conventional crystalline genistein after 6 months storage at room temperature, such as the reduced bioavailability of the active ingredient to the skin and the risk for the cosmetic consumer to perceive their presence upon application to the skin. As illustrated by FIG. 1, which shows a microscopical examination of formulation #1 with stabilized nanoparticles of genistein after 6 months storage at room temperature, the same cosmetic preparation with stabilized nanoparticles of genistein is perfectly stable, even after storage of 6 months at room temperature.

EXAMPLE 9

O/W emulsions with different genistein forms

| Ingredients | #3 % (w/w) | #4 % (w/w) |
|---|---|---|
| Glyceryl Myristate | 4.00 | 4.00 |
| Cetyl Alcohol | 2.00 | 2.00 |
| Steareth-2 | 2.00 | 2.00 |
| Steareth-21 | 2.00 | 2.00 |
| Isopropyl Myristate | 5.00 | 5.00 |
| Caprylic/Capric Triglyceride | 8.00 | 8.00 |
| BHT | 0.05 | 0.05 |
| Dimethicone | 2.00 | 2.00 |
| Phenoxyethanol & Methylparaben & Ethylparaben & Butylparaben & Propylparaben & Isobutylparaben | 0.80 | 0.80 |
| Aqueous suspension of genistein nanoparticles (contains 5.5% genistein approx. 0.4 microns) | 5.45 | — |
| Genistein (crystalline, approx. 12 microns) | — | 0.30 |
| Water | Ad. 100 | Ad. 100 |
| Propylene Glycol | 4.00 | 4.00 |

-continued

O/W emulsions with different genistein forms

| Ingredients | #3 % (w/w) | #4 % (w/w) |
|---|---|---|
| Polyacrylamide & C13-14 Isoparaffin & Laureth-7 | 1.00 | 1.00 |
| Potassium Hydroxide (10%) | 0.15 | 0.15 |
| Disodium EDETA | 0.10 | 0.10 |

Figure 3:
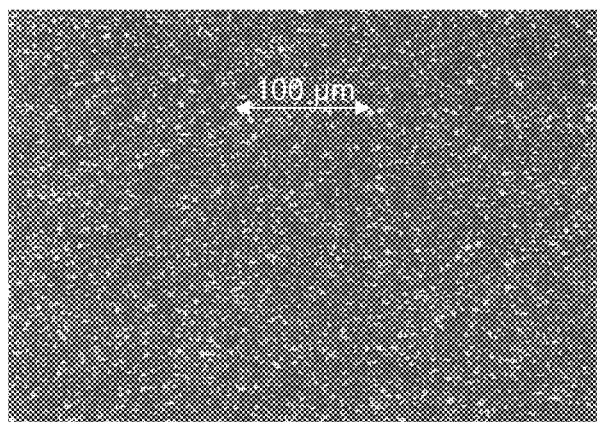
FIGS. 3 and 4 are photomicrographs of formulations after 19 days storage at 24 hour temperature cycles at each of 5° C. and 43° C. temperatures which employ stabilized nanoparticles of genistein according to an embodiment of the invention and conventional genistein as described below in Example 9 by formulations #3 and #4, respectively.

To further illustrate the benefits obtained with nanoparticles of genistein versus conventional crystalline genistein, the cosmetic formulations described above (#3 and #4) were submitted to a very challenging stability test: The formulations were stored at a temperature varying from 5° C. to 43° C. every 24 hours during 3 weeks. The appearance of the formulations was observed under a microscope and is illustrated by FIG. 3, which shows a microscopical examination of formulation #3 with stabilized nanoparticles of genistein after 19 days storage at 5° C./43° C. (cycles of 24 hours at each temperature), and FIG. 4, which shows a microscopical examination of formulation #4 with conventional crystalline genistein after 19 days storage at 5° C./43° C. (cycles of 24 hours at each temperature).

Figure 4:
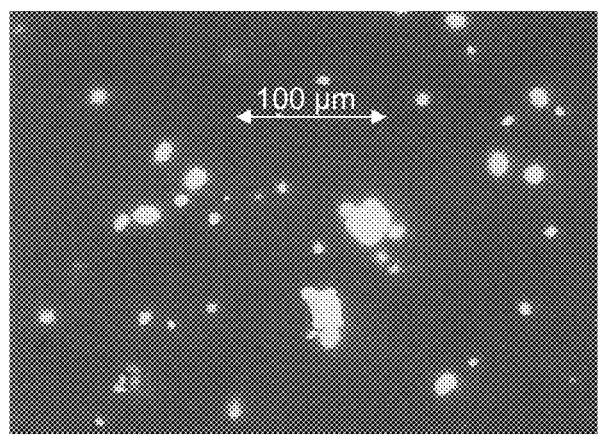

As illustrated by FIG. 3 the nanoparticles of genistein are still very finely dispersed in the cosmetic preparation, contrary to FIG. 4 which illustrates that conventional crystalline genistein in the same preparation has formed large crystals.

EXAMPLE 10

To force the crystallization in a disperse system, a test was used in which the temperature is changed over a self-defined timeframe and in self-defined sequences. The test is called "swing" test (changing temperature test). The purpose of this test is to dissolve small particles at the higher temperature and to force re-crystallization at lower temperature. But it is also a stress testing method which shows if a formulation is stable. The following formulations were used for the "swing" test:

| Pos. | Ingredient | Content |
|---|---|---|
| o | Caprylic/Capric Triglyceride | 8.00% |
| o | Isopropyl Myristate | 5.00% |
| o | Glyceryl Myristate | 4.00% |
| o | Cetyl Alcohol | 2.00% |
| o | Dimethicone | 2.00% |
| o | Steareth-2 | 2.00% |
| o | Steareth-21 | 2.00% |
| o | Phenoxyethanol & Methylparaben & Ethylparaben & Butylparaben | 0.80% |
| o | BHT | 0.05% |
| w | Water dem. | ad 100% |
| w | Propylene Glycol | 4.00% |
| w | Edeta BD | 0.10% |
| t | Polyacrylamide & C13-14 Isoparaffin & Laureth-7 | 1.00% |
| g | Genistein | 0.1%-1.0% |
| b | Potassium Hydroxide 10% solution | 0.15% |

Manufacturing Specifications:

Oil- and water phase (o+w) were separately heated up to 70° C. (5° C.) and were added together. The thickening agent (t) was added under moderate agitation. The mixture was homogenized for 30 seconds at 24'000 RPM by means of an Ultra-Turrax T25 homogenizer. The emulsion was cooled down slowly to 45° C.±5° C. under moderate stirring (horseshoe mixer, 120 RPM). At this temperature the pH value was adjusted to pH 6.5-7.0 by adding base (b). Genistein (g) was added to the still fluid emulsion and was incorporated by homogenizing again for 30 sec. 24'000 RPM by means of an Ultra-Turrax T25 homogenizer. The formulation was cooled down to 25° C.±5° C. under moderate stirring (horseshoe mixer, 120 RPM).

Standard Stability Assessment:

As a standard stability test the following conditions were used: the formulated cosmetic samples were stored: 5° C.±2° C., ambient temperature (e.g. 20-25° C.) and 43° C.±2° C. with checkpoints after 2 weeks, 6 weeks, 3 months, 6 months and 12 months. A few samples show crystal growth not before 3 months, which means that a long period goes by where no statement of future morphologic stability can be made.

Stability Assessment by "Swing" Test:

To force this crystallization the "swing" test was used and as minimum and maximum temperatures 5° C. and 43° C. were chosen. Each temperature was held over a period of 24 hours. The duration of this test was at first set to 20 days, which means that the samples run through a cooling/heating sequence (=1 sequence) 10 times.

Figure 5A:
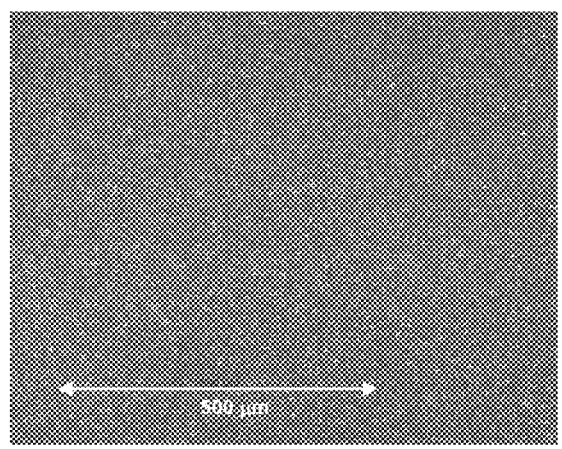
FIGS. 5(a)-5(c) show the results of the "swing" test for formulations as described in Example 3 below at concentrations of 0.3%, 0.5% and 1.0%, respectively.
Figure 5B:
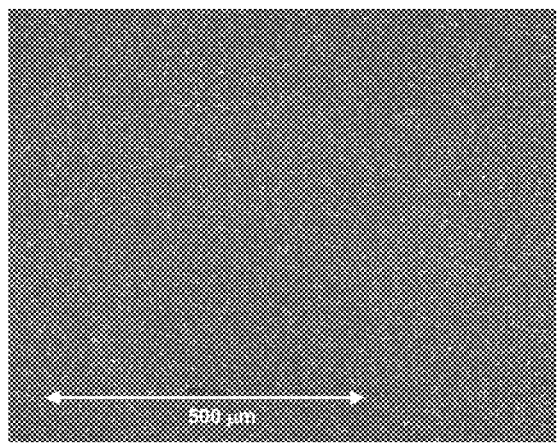
Figure 5C:
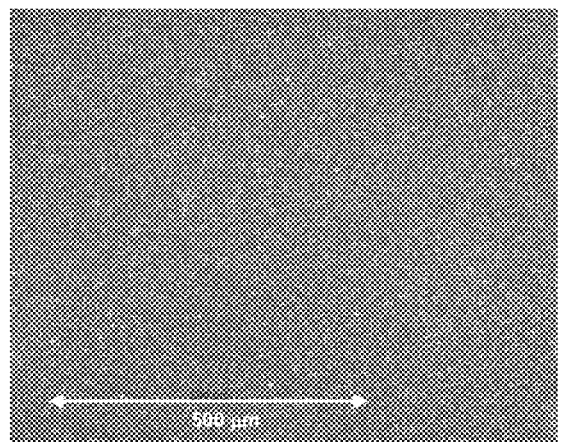
Figure 6A:
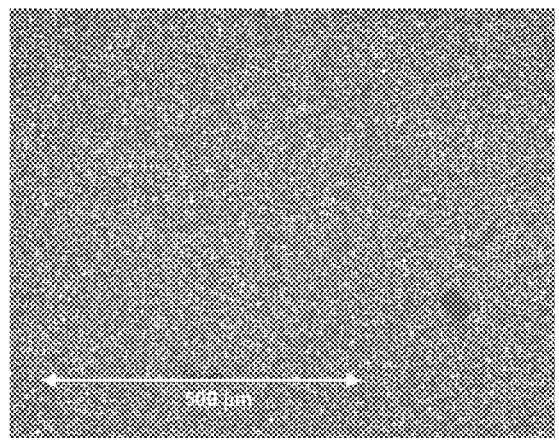
FIGS. 6(a)-6(c) show the results of the "swing" test for formulations as described in Example 6 below at concentrations of 0.3%, 0.5% and 1.0%, respectively.
Figure 6B:
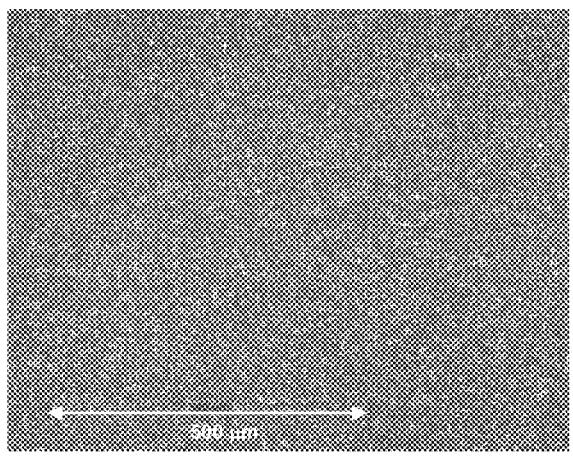
Figure 6C:
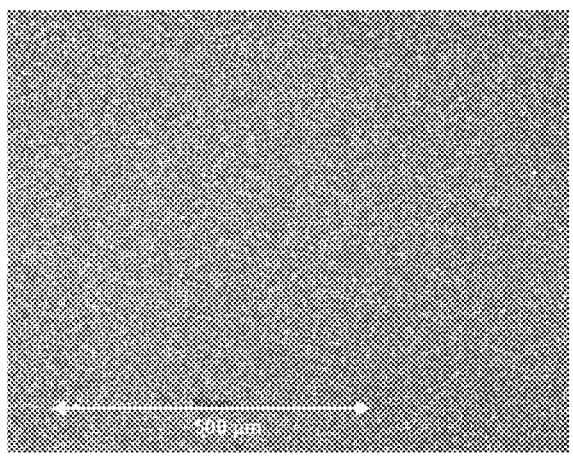
Figure 7A:
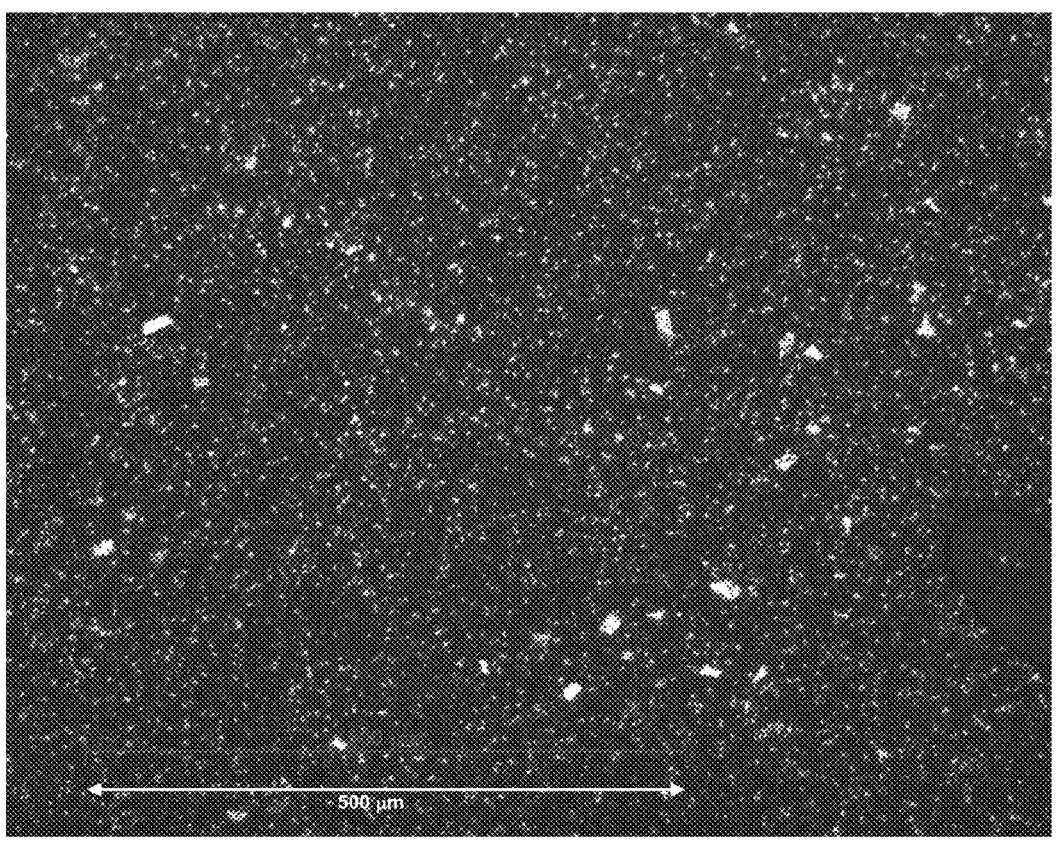
FIGS. 7(a)-7(c) show the results of the "swing" test for formulations as described in Example 7 below after dry grinding in a Jet mill in a concentration of 0.3%, 0.5% and 1.0%, respectively.
Figure 7B:
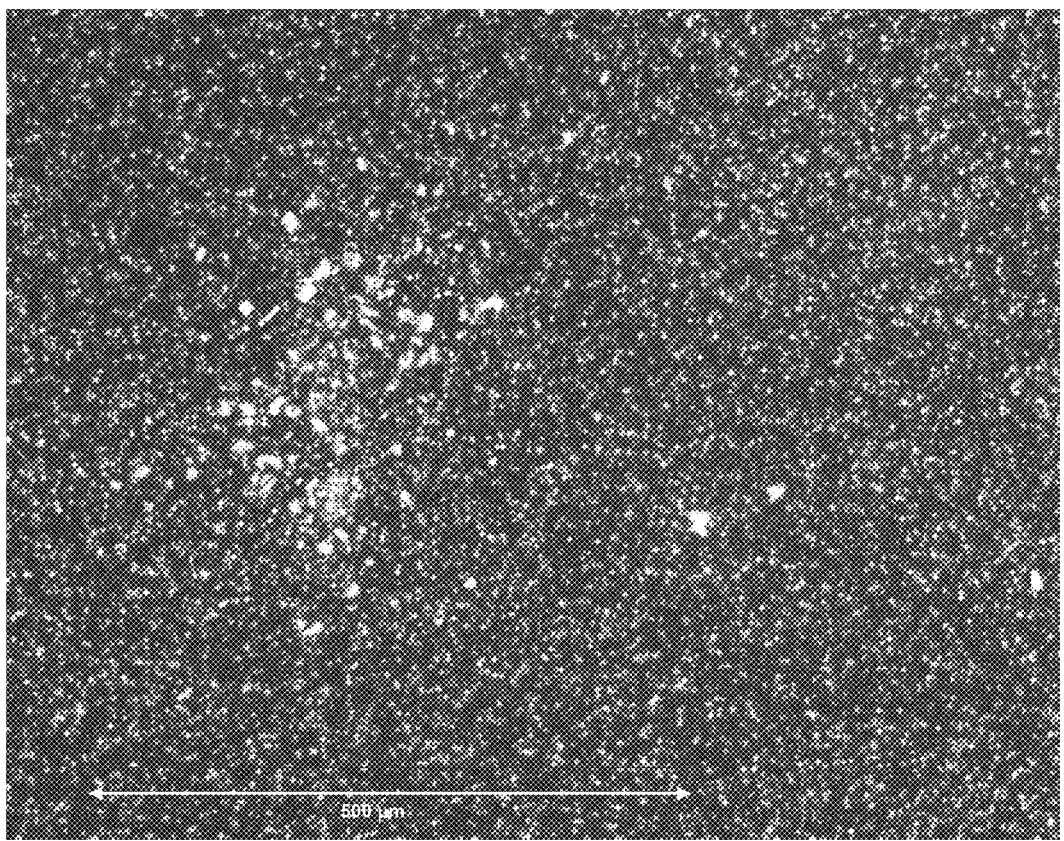
Figure 7C:
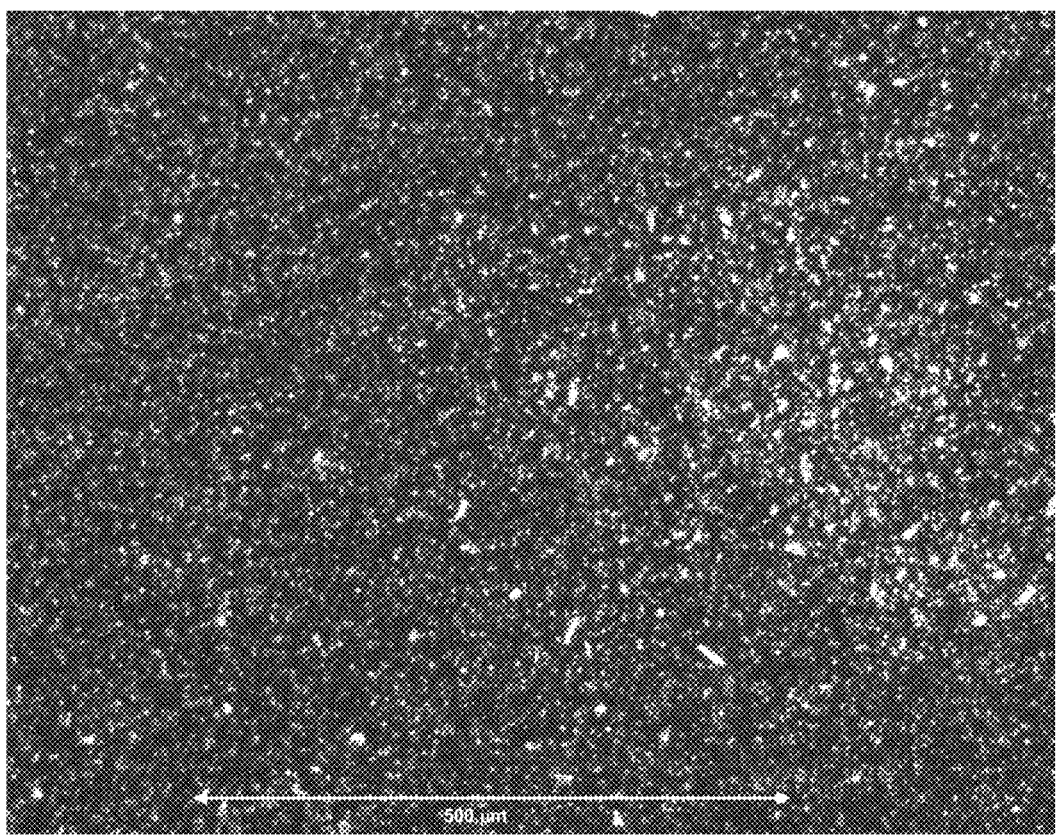

FIGS. 5 to 7 show the results of the "swing" test. Genistein-containing emulsions where prepared as described above using the genistein nanoparticle compositions as described below. The following genistein samples and concentrations were employed and the emulsions were measured immediately after preparation and after subjecting the samples to ten sequences of the "swing" test:

FIG. 5(*a*): Composition of example 3 in a concentration of 0.3%

FIG. 5(*b*): Composition of example 3 in a concentration of 0.5%

FIG. 5(*c*): Composition of example 3 in a concentration of 1.0%

FIG. 6(*a*): Composition of example 6 in a concentration of 0.3%

FIG. 6(*b*): Composition of example 6 in a concentration of 0.5%

FIG. 6(*c*): Composition of example 6 in a concentration of 1.0%

FIG. 7(*a*): Composition of example 7, after dry grinding in a Jet mill in a concentration of 0.3%

FIG. 7(*b*): Composition of example 7 after dry grinding in a Jet mill in a concentration of 0.5%

FIG. 7(*c*): Composition of example 7 after dry grinding in a Jet mill in a concentration of 0.1%

FIG. 8(*a*): Composition of example 7 final product as described in example 7 in a concentration of 0.3%

FIG. 8(*b*): Composition of example 7 final product as described in example 7 in a concentration of 0.5%

FIG. 8(*c*): Composition of example 7 final product as described in example 7 in a concentration of 1.0%.

The magnification was the same in all figures, and a distance of 500 µm is indicated in FIG. 5(*a*).

It can be seen that even under the severe conditions of the "swing" test the topical cosmetic compositions of the present invention do not show any increase in the particle size, even in very high concentrations of 0.3 to 1.0%. The "swing" test in fact had no effect on the particle size or the particle distribution.

Contrary thereto, in FIG. 7, where genistein was used before milling or homogenization, the particle size significantly changed during the "swing" test. Huge crystals are formed and clusters of crystals can be seen after ten sequences.

The invention claimed is:

1. A topical composition comprising an isoflavone nanoparticle composition comprised of nanoparticles consisting of crystalline isoflavone, the nanoparticles having an average particle size D[4,3] as determined by laser diffraction technique of less than 3 μm, wherein the average particle size of the nanoparticles in the composition remains substantially constant after subjecting the composition to ten 24-hour heating and cooling sequences between 5° C. to 43° C.

2. The topical composition according to claim 1, wherein the isoflavone nanoparticle composition further comprises at least one carrier.

3. The topical composition according to claim 1, wherein the nanoparticles have an average particle size D[4,3] as determined by laser diffraction technique of 1 micron or less.

4. The topical composition according to claim 3, wherein the nanoparticles have an average particle size D[4,3] as determined by laser diffraction technique of 0.5 micron or less.

5. The topical composition according to claim 3, wherein the nanoparticles have an average particle size D[4,3] as determined by laser diffraction technique of 0.05 micron or more.

6. The topical composition according to claim 2, wherein the carrier is selected from carbohydrates, proteins and mixtures thereof.

7. The topical composition according to claim 6, wherein the carbohydrate is selected from modified starch, sorbitol, maltose, maltodextrin, gum acacia, pectin, alginate, guar gum, xanthan, cellulose derivatives and mixtures thereof.

8. The topical composition according to claim 6, wherein the protein is selected from gelatin, milk protein, soy protein and mixtures thereof.

9. The topical composition according to claim 1, which is a topical pharmaceutical or cosmetic composition.

10. The topical composition according to claim 9, which is a cosmetic composition.

11. The topical composition according to claim 1, which contains the nanoparticles in a concentration of 0.01 wt.-% or more based on the weight of the composition.

12. The topical composition according to claim 11, which contains the nanoparticles in a concentration of 0.3 wt.-% or more based on the weight of the composition.

13. The topical composition according to claim 1, wherein the isoflavone is genistein.

14. The topical composition according to claim 1, wherein the composition is free of ethanol.

15. A method of preparing a topical composition comprising incorporating into a topical carrier an isoflavone nanoparticle composition as defined in claim 1.

16. The method according to claim 15, wherein the isoflavone is genistein.

17. The method according to claim 15, wherein the topical composition is a topical cosmetic composition or a topical pharmaceutical composition.

18. The method according to claim 17, wherein the topical cosmetic or topical pharmaceutical composition is for achieving a beautifying effect on human skin, an anti-aging or an anti-wrinkle effect, for skin lightening, for protection against UV-radiation damages or for repair of damaged skin.

19. The method according to claim 17, wherein the topical cosmetic or topical pharmaceutical composition is for achieving an increased or prolonged effect for beautifying human skin, an anti-aging or an anti-wrinkle effect, for achieving skin lightening, for protection against UV-radiation damages.

20. The method according to claim 18, wherein the topical cosmetic composition or topical pharmaceutical composition is for treating skin aging.

21. The method according to claim 15, wherein the topical composition is for providing an antibacterial activity.

22. An isoflavone nanoparticle composition, consisting essentially of (i) nanoparticles which consist of crystalline isoflavone, (ii) a carrier and (iii) water, wherein the carrier is a hydrophobically modified starch and the nanoparticles of the nanoparticle composition have an average particle size D[4,3] as determined by laser diffraction of less than 3 μm, and wherein the average particle size of the nanoparticles in the composition remains substantially constant after subjecting the nanoparticle composition to ten 24-hour heating and cooling sequences between 5° C. to 43° C.

23. An isoflavone nanoparticle composition according to claim 22, wherein the isoflavone is genistein.

24. An isoflavone nanoparticle composition according to claim 22, containing 10 to 30% of isoflavone, 15 to 40% of the carrier, the rest being water.

25. Process for producing an isoflavone nanoparticle composition as defined in claim 22, wherein an aqueous suspension of the isoflavone and the carrier is subjected to fragmentation in an agitated bead mill by wet grinding.

26. Process according to claim 25, wherein $ZrO_2$-type grinding media are used.

* * * * *